US012761222B2

(12) United States Patent
Marr et al.

(10) Patent No.: US 12,761,222 B2
(45) Date of Patent: Oct. 13, 2026

(54) METHODS AND COMPOSITIONS USING EXTRACELLULAR VESICLES FOR THE DETECTION OF DISEASE AND DISORDERS

(71) Applicant: PEARL DIAGNOSTICS, INC., Baltimore, MD (US)

(72) Inventors: Kieren Anne Marr, Baltimore, MD (US); Kausik Datta, Baltimore, MD (US); Janet F. Staab, Baltimore, MD (US)

(73) Assignee: PEARL DIAGNOSTICS, INC., Baltimore, MD (US)

( * ) Notice: Subject to any disclaimer, the term of this patent is extended or adjusted under 35 U.S.C. 154(b) by 815 days.

(21) Appl. No.: 17/604,167

(22) PCT Filed: Apr. 15, 2020

(86) PCT No.: PCT/US2020/028276
§ 371 (c)(1),
(2) Date: Oct. 15, 2021

(87) PCT Pub. No.: WO2020/214675
PCT Pub. Date: Oct. 22, 2020

(65) Prior Publication Data

US 2022/0206000 A1 Jun. 30, 2022

Related U.S. Application Data

(60) Provisional application No. 62/833,957, filed on Apr. 15, 2019.

(51) Int. Cl.
*A61K 35/12* (2015.01)
*G01N 33/569* (2006.01)

(52) U.S. Cl.
CPC ... *G01N 33/56961* (2013.01); *G01N 2333/38* (2013.01)

(58) Field of Classification Search
None
See application file for complete search history.

(56) References Cited

U.S. PATENT DOCUMENTS

| | | | |
|---|---|---|---|
| 5,149,632 | A | 9/1992 | Notermans et al. |
| 9,915,657 | B2 | 3/2018 | Marr et al. |
| 10,585,098 | B2 | 3/2020 | Marr |
| 2005/0074410 | A1 | 4/2005 | Crameri et al. |
| 2014/0315195 | A1 | 10/2014 | Wong et al. |
| 2016/0222456 | A1 | 8/2016 | Yamamoto et al. |
| 2016/0320390 | A1 | 11/2016 | Newman et al. |
| 2017/0369930 | A1 | 12/2017 | Jee et al. |
| 2018/0156797 | A1 | 6/2018 | Marr |
| 2021/0364515 | A1 | 11/2021 | Marr |
| 2025/0138009 | A1 | 5/2025 | Marr |

FOREIGN PATENT DOCUMENTS

| | | | |
|---|---|---|---|
| EP | 1104768 | A1 | 6/2001 |
| EP | 3095880 | | 11/2016 |
| EP | 3095880 | A1 | 11/2016 |
| EP | 3955939 | A4 | 2/2023 |
| KR | 1020160150068 | A | 12/2016 |
| WO | WO-2007015177 | A2 | 2/2007 |
| WO | WO-2011063395 | A3 | 10/2011 |
| WO | WO-2015112382 | A1 | 7/2015 |
| WO | 2017/149206 | | 9/2017 |
| WO | WO-2017149206 | A1 | 9/2017 |
| WO | 2017/211906 | A1 | 12/2017 |
| WO | 2018/208977 | A1 | 11/2018 |
| WO | WO-2020214675 | A1 | 10/2020 |

OTHER PUBLICATIONS

Examination Report dated Feb. 9, 2024, of counterpart Canadian Patent Application No. 3,137,017.
Notice of Reasons for Rejection dated Feb. 13, 2024, of counterpart Japanese Patent Application No. 2021-561684 and a machine generated translation.
International Preliminary Report on Patentability from corresponding International Patent Application No. PCT/US2020/028276 dated Oct. 28, 2021.
Wesener, Darryl A., et al., "Recognition of microbial glycans by human intelectin-1", Nature Structural & Molecular Biology, vol. 22, No. 8, Jul. 6, 2015, pp. 603-613.
Kosanovic, Maja, et al., "Isolation of urinary extracellular vesicles from Tamm-Horsfall protein-depleted urine and their application in the development of a lectin-exosome-binding assay", Biotechniques, vol. 57, No. 3, 1 Sep. 2014, pp. 143-149.
Peres Da Silva, Roberta, et al., "Extracellular vesicles from Paracoccidioides pathogenic species transport polysaccharide and expose ligands for DC-SIGN receptors", Scientific Reports, vol. 5, No. 1, Sep. 21, 2015, 12 pgs.
Vallejo, Milene, et al., "The Pathogenic Fungus Paracoccidioides brasiliensis Exports Extracellular Vesicles Containing Highly Immunogenic a-Galactosyl Epitopes", Eukaryotic Cell, Mar. 2011, p. 343-351, vol. 10, No. 3.

(Continued)

*Primary Examiner* — Jennifer E Graser
(74) *Attorney, Agent, or Firm* — Wilson Sonsini Goodrich & Rosati

(57) ABSTRACT

Disclosed herein are methods for detecting a biological or chemical entity in a sample, wherein the biological or chemical entity is associated with extracellular vesicles. The methods disclosed comprise the steps of a) processing the sample, (b) using a detection assay to detect the presence of extracellular vesicles and to isolate the extracellular vesicles, (c) processing the extracellular vesicles to expose or release the biological or chemical entity, and (e) detecting the biological or chemical entity released from the extracellular vesicle. In certain embodiments, the extracellular vesicles are associated with proteins, glycoproteins, peptides, lipids, nucleic acids or other cellular components. The detection methods are useful for identifying the presence of microbial antigens related to *Streptococcus pneumoniae, Aspergillus* species, *Fusarium* species, *Coccidioides* species, *Cryptococcus* species, and *Histoplasma* species.

14 Claims, 12 Drawing Sheets

Specification includes a Sequence Listing.

(56) References Cited

OTHER PUBLICATIONS

Tsuji, Shoutaro, et al., "Human Intelectin Is a Novel Soluble Lectin That Recognizes Galactofuranose in Carbohydrate Chains of Bacterial Cell Wall", The Journal of Biological Chemistry, vol. 276, No. 26, Jun. 1, 2001, pp. 23456-23463.
Extended European Search Report Issued On Jan. 5, 2023 For Corresponding European Patent Application No. 20790631.4.
Search Report and Written Opinion dated Oct. 9, 2023, from corresponding Singapore Application No. 11202111155R.
Kuipers M.E. et al., "Pathogen-Derived Extracellular Vesicle-Associated Molecules That Affect the Host Immune System: An Overview", *Frontiers in Microbiology*, Sep. 12, 2018, vol. 9, Article 2182, 13 pages.
Dufresne S.F., et al., "Detection of Urinary Excreted Fungal Galactomannanlike Antigens for Diagnosis of Invasive Aspergillosis", *PLoS One* (online), Aug. 10, 2012, vol. 7, Issue 8, Article e42736.
International Search Report and Written Opinion from corresponding International Patent Application No. PCT/US2020/028276 dated Aug. 6, 2020.
Examination Report dated Feb. 19, 2025, from corresponding European Patent Application No. 20790631.4.
Notice of Reasons for Refusal dated Nov. 12, 2024, from counterpart JP Application No. 2021-561684.
Second Written Opinion dated Aug. 21, 2025, from counterpart Singapore Patent Application No. 11202111155R.
De Toro, Julieta et al.: Emerging roles of exosomes in normal and pathological conditions: new insights for diagnosis and therapeutic applications. Frontier in Immunology 6:203 (2015). https://doi.org/10.3389/fimmu.2015.00203.
Saad, Mabroka H. et al.: A Comprehensive Insight into the Role of Exosomes in Viral Infection: Dual Faces Bearing Different Functions. Pharmaceutics 3:1405 (2021). https://doi.org/10.3390/pharmaceutics 13091405.
Abad, Ana et al.: What makes Aspergillus fumigatus a successful pathogen? Genes and molecules involved in invasive aspergillosis. Revista Iberoamericana de Micología 27(4):155-182 (Oct.-Dec. 2010) (English Abstract).
Alano, Alexandre: Challenges in microbiological diagnosis of invasive Aspergillus infections. F1000Research 2017, 6(F1000 Faculty Rev):157, pp. 1-10, Last updated: Nov. 14, 2024.
Bennett, John E. et al.: Receptor-Mediated Clearance of Aspergillus Galactomannan. The Journal of Infectious Diseases 155(5):1005-1010 (May 1987), https://doi.org/10.1093/infdis/155.5.1005 (Abstract).
Completo, Gladys et al.: Synthesis of galactofuranose-containing acceptor substrates for mycobacterial galactofuranosyltransferases. Journal of Organic Chemistry 73:4513-4525 (2008). 10.1021/jo800457j.
Domenech, Jezabel et al.: Galactomannans from the cell walls of species of *Paecilomyces* sect. Paecilomyces and their teleomorphs as immunotaxonomic markers. Microbiology 145:2789-2796 (1999).
Duettman, Wiebke et al.: Serum and urine galactomannan testing for screening in patients with hematological malignancies. Medical Mycology 52(6):647-652 (Aug. 2014), https://doi.org/10.1093/mmy/myu019 (abstract).
Dufresne, Simon F. et al.: Detection of Urinary Excreted Fungal Galactomannan-like Antigens for Diagnosis of Invasive Aspergillosis, PLOS One 7(8):e42736, Aug. 10, 2012, pp. 1-10, https://doi.org/10.1371/journal.pone.0042736.
Dupont, Bertrand et al.: Galactomannan Antigenemia and Antigenuria in Aspergillosis: Studies in Patients and Experimentally Infected Rabbits. The Journal of Infectious Diseases 155(1):1-11 (Jan. 1987), https://doi.org/10.1093/infdis/155.1.1.
Engel, Jakob et al.: A single UDP-galactofuranose transporter is required for galactofuranosylation in Aspergillus fumigatus. The Journal of Biological Chemistry 284(49):3859- 33868 (Dec. 2009).
European Examination Report dated Dec. 5, 2025 issued in European Patent Application No. 20790631.4.
Haynes, K.A. et al.: Detection of Aspergillus antigens associated with invasive infection. ASM Journals / Journal of Clinical Microbiology 28(9):2040-2044 (Sep. 1990).
Katafuchi, Yukako et al.: GfsA is a β1,5-galactofuranosyltransferase involved in the biosynthesis of the galactofuran side chain of fungal-type galactomannan in Aspergillus fumigatus. Glycobiology 27(6):568-581 (Jun. 2017), https://doi.org/10.1093/glycob/cwx028 (Abstract).
Klont, Rocus et al.: Utility of Aspergillus antigen detection in specimens other than serum specimens. Clinical Infectious Diseases, 39(10):1467-1474 (Nov. 2004), https://doi.org/10.1086/425317 (Abstract).
Komachi, Yuji et al.: GfsA encodes a novel galactofuranosyltransferase involved in biosynthesis of galactofuranose antigen of O-glycan in Aspergillus nidulans and Aspergillus fumigatus. Molecular Microbiology 90(5):1054-1073 (2013). doi:10.1111/mmi.12416.
Krylov, Vadim B. et al.: Reinvestigation of carbohydrate specificity of EB-A2 monoclonal antibody used in the immune detection of Aspergillus fumigatus galactomannan. Heliyon 5(1):e01173 (Jan. 2019), 9 pages.
Kudoh, Atsushi et al.: Significant structural change in both O- and N-linked carbohydrate moieties of the antigenic galactomannan from Aspergillus fumigatus grown under different culture conditions. Glycobiology 25(1):74-87 (Jan. 2015), https://doi.org/10.1093/glycob/cwu091 (Abstract).
Laboatories B-R, Bio-Rad Laboratories, Platelia Aspergillus EIA, 2009, 22 pages.
Latge, Jean-Paul et al.: Chemical and immunological characterization of the extracellular galactomannan of Aspergillus fumigatus. ASM Journals Infection and Immunity 62(12):5424-5433 (Dec. 1994).
Latge, Jean-Paul: Galactofuranose containing molecules in Aspergillus fumigatus. Medical Mycology 47(Supplement_1):S104-S109 (2009), https://doi.org/10.1080/13693780802258832 (Abstract).
Leeflang, MMG et al.: Galactomannan detection for invasive aspergillosis in immunocompromised patients (Review). Cochrane Database of Systematic Reviews 2015, Issue 12. Art. No. CD007394. DOI: 10.1002/14651858.CD007394.pub2.
Lehmbecher, Thomas et al.: Diagnostic Approaches for Invasive Aspergillosis-Specific Considerations in the Pediatric Population. Frontier in Biology 9(518):1-8 (Mar. 2018).
Marques Souza, Jéssica Amanda et al.: Characterization of Aspergillus fumigatus Extracellular Vesicles and Their Effects on Macrophages and Neutrophils Functions. Frontiers in Microbiology 10: 1-13 (Sep. 2019). https://doi.org/10.3389/fmicb.2019.02008.
Marr, Kieren A. et al.: Antifungal therapy decreases sensitivity of the Aspergillus galactomannan enzyme immunoassay. Clinical Infectious Diseases 40(2):1762-1769 (Jun. 2005) Abstract. https://doi.org/10.1086/429921.
Marr, Kieren A. et al.: Urine Antigen Detection as an Aid to Diagnose Invasive Aspergillosis. Clinical Infectious Diseases 67(11):1705-1711 (Dec. 2018), https://doi.org/10.1093/cid/ciy326.
Mengoli, Cruciani et al.: Polymerase chain reaction blood tests for the diagnosis of invasive aspergillosis in immunocompromised people. Cochrane Database of Systematic Reviews 2019, Issue 9. Art. No. CD009551. DOI: 10.1002/14651858.CD009551.pub4.
Mennink-Kersten, Monique A.S.H. et al.: In Vitro Release by Aspergillus fumigatus of Galactofuranose Antigens, 1,3-β-d-Glucan, and DNA, Surrogate Markers Used for Diagnosis of Invasive Aspergillosis. Journal of Clinical Microbiology 44(5):1711-1715 (May 20026). https://doi.org/10.1128/jcm.44.5.1711-1718.2006.
PCT/US2010/057819 International Search Report and Written Opinion dated Aug. 18, 2021 (publication No. WO2011063395).
PCT/US2020/028276 International Search Report and Written Opinion dated Aug. 6, 2020 (publication WO2020214675).
Peres Da Silva, Roberta et al.: Extracellular vesicle-mediated export of fungal RNA. Scientific Reports 5(7763):1-12 (2015). DOI: 10.1038/srep07763.
Pini, P. et al.: Clinical performance of a commercial real-time PCR assay for Aspergillus DNA detection in serum samples from high-risk patients: comparison with a galactomannan enzyme immunoas-

(56) References Cited

OTHER PUBLICATIONS say. European Journal of Clinical Microbiology and Infectious Diseases, Heidelberg 34(1):131-136 (Jan. 2015). DOI:10.1007/s10096-014-2211-y.
Pisitkun, Trairak et al.: Discovery of urinary biomarkers. Molecular & Cellular Proteomics 5(10):1760-1771 (Oct. 2006). https://doi.org/10.1074/mcp.R600004-MCP200.
Rogers, T.R. et al.: Value of antigen detection in predicting invasive pulmonary aspergillosis. The Lancet 336(8725):1210-1213 (Nov. 17, 1990), (abstract and overview).
Schmalhorst, Philipp S. et al.: Contribution of galactofuranose to the virulence of the opportunistic pathogen Aspergillus fumigatus. Eukaryotic Cell 7(8):1268-1277 (Aug. 2008).
Tefsen, Boris et al.: Galactofuranose in eukaryotes: aspects of biosynthesis and functional impact. Glycobiology 22(4):456-469 (Apr. 2012), https://doi.org/10.1093/glycob/cwr144 (Abstract).
U.S. Appl. No. 61/263,498 dated Nov. 23, 2009.
U.S. Appl. No. 13/511,264 Notice of Allowance dated Dec. 26, 2018.
U.S. Appl. No. 13/511,264 Office Action dated Jul. 14, 2015.
U.S. Appl. No. 13/511,264 Office Action dated Mar. 21, 2016.
U.S. Appl. No. 14/546,830 Notice of Allowance dated Jan. 24, 2018.
U.S. Appl. No. 14/546,830 Office Action dated Apr. 13, 2017.
U.S. Appl. No. 14/546,830 Office Action dated Sep. 7, 2016.
U.S. Appl. No. 15/882,278 Notice of Allowance dated Sep. 13, 2019.
U.S. Appl. No. 15/882,278 Office Action dated Feb. 19, 2019.
U.S. Appl. No. 15/882,278 Office Action dated Jun. 10, 2019.
U.S. Appl. No. 16/750,720 Notice of Allowance dated Jun. 29, 2021.
U.S. Appl. No. 16/750,720 Office Action dated Sep. 9, 2020.
U.S. Appl. No. 17/388,733 Office Action dated Feb. 1, 2023.
Vallejo, Jesus G.: Role of Toll-like receptors in cardiovascular diseases. Clinical Science 121:1-10 (2011). doi:10.1042/CS20100539.
Vena, A. et al.: The misleading effect of serum galactomannan testing in high-risk haematology patients receiving prophylaxis with micafungin. Clinical Microbiology and Infection 23(12):1000.e1-1000.e4 (Dec. 2017).
Yu, Bessie et al.: Use of Immunoblotting To Detect Aspergillus fumigatus Antigen in Sera and Urines of Rats with Experimental Invasive Aspergillosis. Journal of Clinical Microbiology Jul. 1990, pp. 1575-1579.

| Categories | Aspergillus proteins in VU7 | Aspergillus proteins in VU32 |
|---|---|---|
| Dehydrogenases | • Metabolism of steroids, cofactors, carbohydrates, lipids, aromatic compounds, amino acids<br>• Dehydrogenases of UNSPECIFIED FUNCTION | • Carbohydrate metabolism |
| DNA Binding Proteins | • Regulator of g-protein coupled signaling<br>• Transcription factor (regulatory protein)<br>• Transcription factor of UNSPECIFIED FUNCTION<br>• Transcription factors, other<br>• Transcription factors for genes required for Galactose & Melibiose catabolism | • Regulator of g-protein coupled signaling<br>• Transcription factor (regulatory protein)<br>• Transcriptional regulatory protein (SpC24 domain)<br>• Transcription factors for genes required for Galactose & Melibiose catabolism |
| Other Enzymes | • L-asparagine synthesis & metabolism<br>• Glycoside hydrolases / carbohydrate metabolism<br>• Transferases<br>• Protease in programmed cell death | • Kinases / Signal transduction<br>• Transferases<br>• Amino acid biosynthesis<br>• UNSPECIFIED FUNCTION (P-loop-NTPase domain) |
| Transport proteins | • Transmembrane transport & metabolism (carbohydrate - fucose) | • Intracellular transport (carbohydrate) & metabolism<br>• Intracellular transport (nuclear)<br>• Intracellular transport (golgi exocytosis) (Av19 domain)<br>• Transmembrane transport & metabolism (carbohydrates)<br>• Transmembrane transport (Fe ion) |
| RNA binding proteins | • Translation of Mitochondrial proteins, Mitochondrial ribosome structure<br>• Translation, ribosome structure | |
| DNA repair proteins | | • DNA replication-recombination-repair enzymes (Pfs & Cdc6 domain) |
| Cell wall remodeling & stress response | • Proteins matching to Aspf7 and Aspf7-like proteins | |

FIG. 3

SEQUENCE LISTING

```
<160> NUMBER OF SEQ ID NOS: 10

<210> SEQ ID NO 1
<211> LENGTH: 339
<212> TYPE: DNA
<213> ORGANISM: Mus musculus
<220> FEATURE:
<221> NAME/KEY: misc_feature
<222> LOCATION: (1)..(339)
<223> OTHER INFORMATION: 205 VH (15A)

<400> SEQUENCE: 1

gaggtgcagc tggaggagtc tctgagactc tcctgtgcaa cttctgggtt caccttcagt     60

gatttctaca tggagtgggt ccgccagcct ccagggaaga gactggagtg gattgctgca    120

agtagaaaca aagctaatga ttatacaaca gagtacagtg catctgtgaa gggtcggttc    180

atcgtctcca gagacacttc ccaaagcatc ctctaccttc agatgaatgc cctgagagct    240

gaggacactg ccatttatta ctgtgcaaga gattactacg gtagtagcta ctggtacttc    300

gatgtctggg gcgcagggac cacggtcacc gtctcctca                           339


<210> SEQ ID NO 2
<211> LENGTH: 341
<212> TYPE: DNA
<213> ORGANISM: Mus musculus
<220> FEATURE:
<221> NAME/KEY: misc_feature
<222> LOCATION: (1)..(341)
<223> OTHER INFORMATION: 205 VL (P1A)

<400> SEQUENCE: 2

gacattctga tgacccagtc tccaactttc cttgctgtga cagcaagtaa gaaggtcacc     60

attagttgca cggccagtga gagcctttat tcaagcaaac acaaggtgca ctacttggct    120

tggtaccaga agaaaccaga gcaatctcct aaactgctga tatacggggc atccaaccga    180

tacattgggg tccctgatcg cttcacaggc agtggatctg ggacagattt cactctgacc    240

atcagcagtg tacaggttga agacctcaca cattattact gtgcacagtt ttacagctat    300

cctctcacgt tcggctcggg gacaaagttg gaaataaaac g                        341


<210> SEQ ID NO 3
<211> LENGTH: 359
<212> TYPE: DNA
<213> ORGANISM: Mus musculus
```

<220> FEATURE:
<221> NAME/KEY: misc_feature
<222> LOCATION: (1)..(359)
<223> OTHER INFORMATION: 24.22.1 VH (PA7)
<220> FEATURE:
<221> NAME/KEY: misc_feature
<222> LOCATION: (18)..(18)
<223> OTHER INFORMATION: n is a, c, g, or t

<400> SEQUENCE: 3
gaggtgcagc tggaggantc tgggggagac ttagtgaagc ctggagggtc cctgaaactc 60
tcctgtgcag cctctggatt cactttcagt agctatggca tgtcttgggt tcgccagact 120
ccagacaaga ggctggagtg ggtcgcaacc attagtagtg gtggtagtta cacctactat 180
ccagacagtg tgaaggggcg attcaccatc tccagagaca atgccaagaa caccctgtac 240
ctgcaaatga gcagtctgaa gtctgaggac acagccatgt attactgtgc aagacttact 300
acggtagtag ctatgctatg gactactggg gtcaaggaac ctcagtcacc gtctcctca 359

<210> SEQ ID NO 4
<211> LENGTH: 341
<212> TYPE: DNA
<213> ORGANISM: Mus musculus
<220> FEATURE:
<221> NAME/KEY: misc_feature
<222> LOCATION: (1)..(341)
<223> OTHER INFORMATION: 24.22.1 VL (B6A)

<400> SEQUENCE: 4
gacattctga tgacccagtc tccaactttc cttgctgtga cagcaagtaa gaaggtcacc 60
attagttgca cggccagtga gagcctttat tcaagcaaac acaaggtgca ctacttggct 120
tggtaccaga agaaaccaga gcaatctcct aaactgctga tatacggggc atccaaccga 180
tacattgggg tccctgatcg cttcacaggc agtggatctg ggacagattt cactctgacc 240
atcagcagtg tacaggttga agacctcaca cattattact gtgcacagtt ttacagctat 300
cctctcacgt tcggtgctgg gaccaagctg gagctgaaac g 341

<210> SEQ ID NO 5
<211> LENGTH: 341
<212> TYPE: DNA
<213> ORGANISM: Mus musculus
<220> FEATURE:
<221> NAME/KEY: misc_feature
<222> LOCATION: (1)..(341)
<223> OTHER INFORMATION: 686.8.5 VH (C5A)

<400> SEQUENCE: 5
gacattctga tgacccagtc tccaactttc cttgctgtga cagcaagtaa gaaggtcacc 60
attagttgca cggccagtga gagcctttat tcaagcaaac acaaggtgca ctacttggct 120
tggtaccaga agaaaccaga gcaatctcct aaactgctga tatacggggc atccaaccga 180
tacattgggg tccctgatcg cttcacaggc agtggatctg ggacagattt cactctgacc 240
atcagcagtg tacaggttga agacctcaca cattattact gtgcacagtt ttacagctat 300
cctctcacgt tcggtgctgg gaccaagctg gagctgaaac g 341

<210> SEQ ID NO 6
<211> LENGTH: 341
<212> TYPE: DNA
<213> ORGANISM: Mus musculus
<220> FEATURE:
<221> NAME/KEY: misc_feature
<222> LOCATION: (1)..(341)

<223> OTHER INFORMATION: 686.8.5 VL (P2A)

<400> SEQUENCE: 6
gacattctga tgacccagtc tccaactttc cttgctgtga cagcaagtaa gaaggtcacc 60
attagttgca cggccagtga gagcctttat tcaagcaaac acaaggtgca ctacttggct 120
tggtaccaga agaaaccaga gcaatctcct aaactgctga tatacggggc atccaaccga 180
tacattgggg tccctgatcg cttcacaggc agtggatctg ggacagattt cactctgacc 240
atcagcagtg tacaggttga agacctcaca cattattact gtgcacagtt ttacagctat 300
ccgctcacgt tcggtgctgg gaccaagctg gagctgaaac g 341

<210> SEQ ID NO 7
<211> LENGTH: 342
<212> TYPE: DNA
<213> ORGANISM: Mus musculus
<220> FEATURE:
<221> NAME/KEY: misc_feature
<222> LOCATION: (1)..(342)
<223> OTHER INFORMATION: 838.9.4 VH (B4B)

<400> SEQUENCE: 7
gaggtgcagc tggaggagtc tctgagactc tcctgtgcaa cttctgggtt caccttcagt 60
gatttctaca tggagtgggt ccgccagcct ccagggaaga gactggagtg gattgctgca 120
agtagaaaca aagctaatga ttatacaaca gagtacagtg catctgtgaa gggtcggttc 180
ttcgtctcca gagacacttc ccaaagcatc ctctaccttc agatgaatgc cctgagagct 240
gaggacactg ccatttatta ctgtgcaaga gatgttatga ttacgacggg ggactggtac 300
ttcgatgtct ggggcgcagg gaccacggtc accgtctcct ca 342

<210> SEQ ID NO 8
<211> LENGTH: 318
<212> TYPE: DNA
<213> ORGANISM: Mus musculus
<220> FEATURE:
<221> NAME/KEY: misc_feature
<222> LOCATION: (1)..(318)
<223> OTHER INFORMATION: 838.9.4. VL (p6)

<400> SEQUENCE: 8
gacattctga tgacccagtc tcaaaaattc atgtccacat cagtaggaga cagggtcagc 60
gtcacctgca aggccagtca gaatgtgggt actaatgtag cctggtatca acagaaacca 120
gggcaatctc ctaaagcact gatttactcg gcatcctacc agtacagtgg agtccctgat 180
cgcttcacag gcagtggatc tgggacagat ttcactctca ccatcagcaa tgtgcagtct 240
gaagacttgg cagagtattt ctgtcagcaa tttaacagct atcacgttcg gctcggggac 300
aaagttggaa ttaaaacg 318

<210> SEQ ID NO 9
<211> LENGTH: 375
<212> TYPE: DNA
<213> ORGANISM: Mus musculus
<220> FEATURE:
<221> NAME/KEY: misc_feature
<222> LOCATION: (1)..(375)
<223> OTHER INFORMATION: 476 VH (P10B-TA)

<400> SEQUENCE: 9
gaggtgcagc tggaggagtc tggaggaggc ttggtacagc ctgggggttc tctgagactc 60
tcctgtgcaa cttctgggtt caccttcagt gatttctaca tggagtgggt ccgccagact 120

-continued

```
ccaggggaga gactggagtg gattgctgca agtagaaaca aagctaatga ttatacagca    180

gaatacagtg cgtctgtgaa gggtcgattc accgtcttta gagacacttc ccaaaacatc    240

ctctaccttc agatgaatgc cctgagagct gaagacactg ccgcctatta ctgtgcaaga    300

gatgcggact acggtaaaac cttttcctgg tacttcgatg tctggggcgc agggaccacg    360

gtcaccgtct catca                                                     375


<210> SEQ ID NO 10
<211> LENGTH: 338
<212> TYPE: DNA
<213> ORGANISM: Mus musculus
<220> FEATURE:
<221> NAME/KEY: misc_feature
<222> LOCATION: (1)..(338)
<223> OTHER INFORMATION: 476 VL (F6A*-TA)

<400> SEQUENCE: 10

gatattgtaa tgacccaaga tgaactctcc aatcctgtca cttctggaga atcagttcac     60

atctcctgca ggtctagtaa gagtctccta tataaggatg ggaagacata cttgaattgg    120

tttctgcaga gaccaggaca atctcctcag ctcctgatct atttgatgtc cacccgtgca    180

tcaggagtct cagaccggtt tagtggcagt gggtcaggaa cagatttcac cctggaaatc    240

agtagagtga aggctgagga tgtgggtgtg tattattgtc aacaacttgt agaatatccg    300

ctcacgttcg gtgctgggac caagctggag ctgaaacg                            338
```

METHODS AND COMPOSITIONS USING EXTRACELLULAR VESICLES FOR THE DETECTION OF DISEASE AND DISORDERS

INCORPORATION-BY-REFERENCE OF MATERIAL SUBMITTED ELECTRONICALLY

The instant application contains a Sequence Listing which has been submitted in ASCII text format via EFS-Web and is hereby incorporated by reference in its entirety. Said ASCII text copy, created on Apr. 20, 2026, is named 72296-704.831.txt and is 6,386 bytes in size.

FIELD OF THE INVENTION

Provided herein are improved methods and compositions useful for detecting infectious organisms and diagnosing associated diseases and disorders.

BACKGROUND OF THE INVENTION

Currently available diagnostic tests for detecting pathogenic organisms and biomarkers indicative of disease and disorder are subject to a variety problems. Oftentimes, such tests require the use of difficult to obtain samples, multi-step sample processing and subsequent analysis that may be dependent upon weak signal detection and prone to human error. An additional complication associated with currently available diagnostic tests is attributable to the evolution of drug resistant microbes that no longer readily display or present antigenic markers that have traditionally been used to detect them. In other instances, pathogens and markers are hidden or masked by proteins, or obstructed by other biological components that inhibit easy detection.

What is needed are improved methods for detecting pathogenic organisms and biomarkers that may be easily applied to readily available samples. What is also needed are methods that include the processing of samples so that elements that may obstruct accurate detection of such pathogenic organisms and biomarkers are removed or prevented from interfering with the ultimate detection procedure.

An example of a currently available, non-culture based diagnostic tests involves the detection of fungal antigens circulating in blood. Two available tests which detect secreted cellular polysaccharides beta.-1,3 glucan (GL) and galactomannan (GM), have inconsistent performance characteristics and require sophisticated and expensive laboratory resources to perform. The sophistication required for laboratory testing and the need for blood draw and/or invasive sampling of bronchoalveolar lavage fluid, limit the application of currently available assays such that screening can be performed only infrequently and require health care facilities for phlebotomy, bronchoscopy and sample processing.

Development of easy-to-use diagnostic tests that involve minimal processing of a sample is highly desirable. Furthermore, the development of tests that can be used on easy to obtain samples such urine, would improve early detection and thereby increase the chances of early intervention to diminish severity of symptoms.

In addition, development of an easy-to-use "point of care" (POC) assay would allow for frequent screening during the period in which a patient is at highest risk for an infection, especially after discharge from a health care facility. Lateral flow devices (LFD), also known as immunochromatographic strip tests, are a common POC testing method. LFDs reduce time spent waiting for test results (from hours to minutes), require less training for operators (thereby enabling user interpretation), and are less expensive both to manufacture and to use.

Certain organisms are notoriously challenging to detect. Fungi, as a group, are polysaccharide-rich organisms, which explains some limited success in the development of antigen-based assays for fungi. However, certain fungal antigens are concentrated in urine. This characteristic, however, has only been exploited for developing diagnostics for relatively rare endemic mycoses (e.g. histoplasmosis) and cryptococcosis.

Galactose is common in mammals, but only found in the 6-member ring hexopyranosyl form, called galactopyranose (galP). Other organisms, including some bacteria, fungi, protozoa, lichens, green algae, starfish and sponges, make galactofuranose (galF), the 5-member ring form of galactose. Equilibrium strongly favors the galP form unless the organism contains specific enzymes to catalyze maintenance of galF. In these organisms, galF is an important residue on glycoconjugate antigens, and can be found linked to secreted and cellular polysaccharides, glycoproteins and glycosphingolipids.

The present inventors previously identified a class of antibodies that were generated against conidia of an important fungal pathogen, called *Aspergillus fumigatus*. These antibodies were found to identify galF antigens that were quickly excreted in urine after infection in mammals. The antibodies and the technology enable their use as a urine diagnostic assay.

What is needed however, are methods for improving diagnosis and optimizing the sensitivity of detection assays, namely improved detection of biological and chemical entities that are associated with pathogenic organisms, and biomarkers. What is also needed are methods that improve sensitivity and performance of such detection assays with minimal sample processing. Furthermore, what is needed are improved diagnostic methods that may be used on easy to obtain samples such as, but not limited to, urine.

SUMMARY OF THE INVENTION

In accordance with one or more embodiments, the present invention provides methods for detecting a biological or chemical entity in a sample, wherein the biological or chemical entity is associated with extracellular vesicles, comprising: processing the sample, using a detection assay to detect the presence of extracellular vesicles and to isolate the extracellular vesicles, processing the extracellular vesicles to expose or release the biological or chemical entity, and detecting the biological or chemical entity released from the extracellular vesicle. The sample may be processed by a variety of methods, including by centrifugation through a column that removes calcium, which fragments uromodulin, enabling co-precipitation of extracellular vesicles that are bound by monomeric uromodulin. Once the extracellular vesicle is isolated, it may be further processed to 'release' the entity to be detected. In certain embodiments, the methods herein enable the identification of extracellular vesicles associated with, or bound within, other precipitable biological components, such as proteins, including, but not limited to uromodulin. Uromodulin is a protein that is primarily found in urine.

In certain embodiments, the methods described herein enable improved galF antigen detection in human body fluids by disabling or otherwise removing a competitive inhibitor, the human lectin, intelectin-1 from the assay process previously disclosed in U.S. patent application Ser.

No. 13/511,264, and by enabling the detection of extracellular vesicles that contain or otherwise associate with galF antigen or other intelectin-recognized ligands. Although extracellular vesicles are known to be secreted by certain microbial cells, and extracellular vesicles are known to be present in urine, it was not known until now that urine contains exogenous extracellular vesicles that in some cases contain antigens of interest such as galF antigen. The present inventors previously demonstrated that intelectin is present in urine, and that it serves to compete with galF-directed antibodies when they are used as part of diagnosing microbial infections in a mammalian subject. This discovery, along with the discovery the galF antigen is associated with extracellular vesicles, allows for the development of detection assays having improved sensitivity and accuracy, and for development of multiplexed assays.

In some embodiments, the methods described herein further encompass the detection of other microbial infections such as those caused by an organism selected from the group consisting of Ascomycetes fungi, *Aspergillus* species, *Fusarium* species, *Coccidioides* species, *Cryptococcus* species, *Zygomycetes* and *Histoplasma* species.

In some embodiments, the microbial infection is caused by an organism having a propensity to cause lung infection, including but not limited to, *Streptococcus pneumoniae*, Gram positive bacterial species, Gram negative bacterial species, including *Pseudomonas* species, *Nocardia* species, *Actinomycetes* fungi, Mycobacteria species as well as fungal organisms such as *Aspergillus* species, *Cryptococcus* species, *Histoplasma* species, *Pneumocystis* species, *Mucorales* species and other *Zygomycetes*. As such, in accordance with one or more embodiments, the present invention provides methods for optimization of galF-antigen identification in fluids that contain intelectin, including urine, respiratory fluids, gastrointestinal fluids, and blood. The present inventors found that this is important for optimizing those methods that specifically focus on fungal antigens. The utility is broadly applicable to diagnostics that target galF containing antigens in many different diagnostic systems, given the ubiquity of galF in microbial antigens.

While the discovery herein is demonstrated in terms that relate and specifically apply to the detection of galF, the inventors contemplate the application of these findings to the detection of antigens other than just galF. For example, it is contemplated that for other microbes, extracellular vesicles may carry the components that are both within the cytoplasm of the organism and expressed on the cell wall, hence including several other antigens. In an embodiment for example, it is possible that that the findings herein are applied to detecting extracellular vesicles containing antigens, or fragments thereof, such as MPB64 associated with *Mycobacterium tuberculosis* for diagnosing tuberculosis. In accordance with an embodiment, the present invention provides a method for diagnosing a microbial infection in a biological sample from a mammalian subject suspected of having, having, or susceptible to having a microbial infection by detecting the presence of at least one polysaccharide comprising a galactofuranose (galF) residue in a biological sample of the mammalian subject, wherein the method comprises: a method for detecting fungal antigens in a urine sample, wherein the fungal antigens are associated with extracellular vesicles, comprising: processing the sample using a desalting column, using a detection assay to detect the presence of extracellular vesicles and to isolate the extracellular vesicles, processing the extracellular vesicles to expose or release the fungal antigens, and detecting the fungal antigens released from the extracellular vesicle. The method further comprises detecting fungal antigens released from the extracellular vesicle comprising contacting the treated sample with at least one antibody specific for at least one polysaccharide or glycoprotein comprising a galactofuranose residue in an effective amount to produce a detectable amount of antibody-polysaccharide complex; and detecting the presence of at least one antibody-polysaccharide complex, wherein the detection of the presence of at least one antibody-polysaccharide complex is diagnostic of the presence of a microbe in the sample; the antibody may comprise mAb476.

In accordance with some embodiments, the method for processing the sample comprises contacting the sample with a substrate which binds or chelates $Ca^{2+}$ ions with high affinity.

In accordance with some embodiments, the method for processing the sample comprises contacting the sample with a compound which eliminates $Ca^{2+}$ ions by size exclusion In accordance with some embodiments, the method for processing the sample comprises contacting the sample with a substrate which binds hIntL with high affinity.

In accordance with some embodiments, the method for processing the sample comprises contacting the sample with one or more compounds which are bound by hINTL with high affinity selected from the group consisting of glycerol, 3-Keto-2-deoxyoctonic acid; D-glycerol-1-phosphate, D-mannoheptose, sepharose, sepharose-containing particles (i.e. latex, polystyrene or glass beads, microspheres or gels.

In accordance with some embodiments, the extracellular vesicles are bound to a protein.

In accordance with some embodiments, the extracellular vesicles are bound to a protein such as uromodulin.

BRIEF DESCRIPTION OF THE DRAWINGS

FIGS. 1A and 1B show that mAb476 reacts stronger with EP than with GM; FIG. 1C shows that mAb476 has novel specificity for polysaccharides in ethanol precipitate (EP) of fungi that produce galF.

FIG. 3 provides mass spectrometric determination of mAb476-reactive proteins with no human homologs in urines from IA subjects, arranged in functional groups-cell wall remodeling, transport, cellulose breakdown, stress response, etc.

FIG. 4A shows that *Aspergillus* EVs measure 50-500 nM by nanoparticle tracking analysis; FIG. 4B shows that mAb476 binds multiple epitopes per EV; FIG. 4C shows that recognition of antigen from EV increases with lysis; FIG. 4D shows that mAb476-reactive EVs in cell wall of dormant conidia; FIG. 4E shows that increased mAb476 binding to germinating conidia; FIG. 4F shows that hyphal wall and extracellular matrix exposes mAb476-bound vesicles (large and small).

FIG. 5A shows that IA subject urines have EVs with wide size distribution; FIG. 5B shows that EVs from case urines separately show surface markers of fungal (top) and human (bottom) origin; FIG. 5C shows that urinary EVs morphologically similar to culture-derived EVs.

DETAILED DESCRIPTION OF THE INVENTION

Figure 1A:
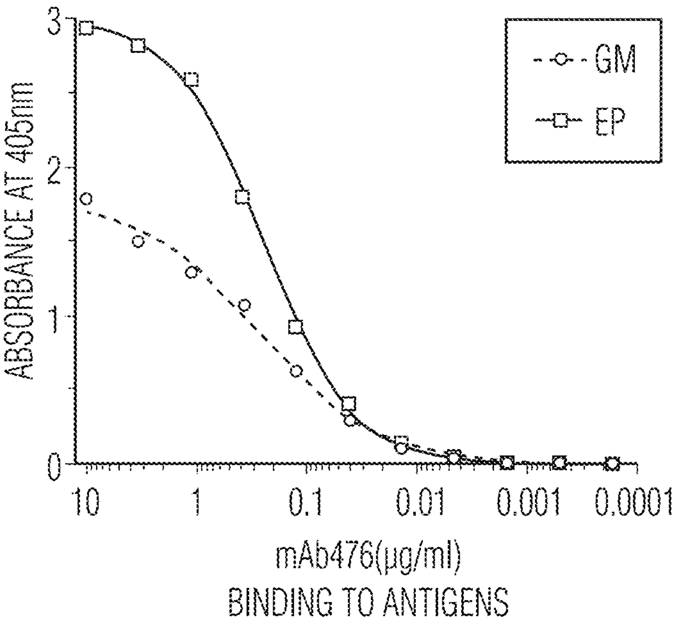
FIGS. 1A-1C provide graphs showing that mAb476 has novel specificity for polysaccharides in ethanol precipitate (EP) of fungi that produce galF.
Figure 1B:
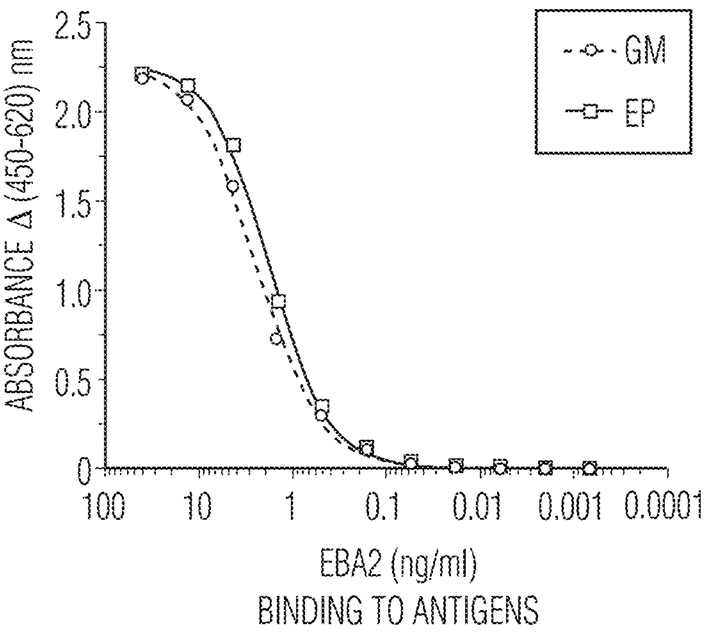
Figure 1C:
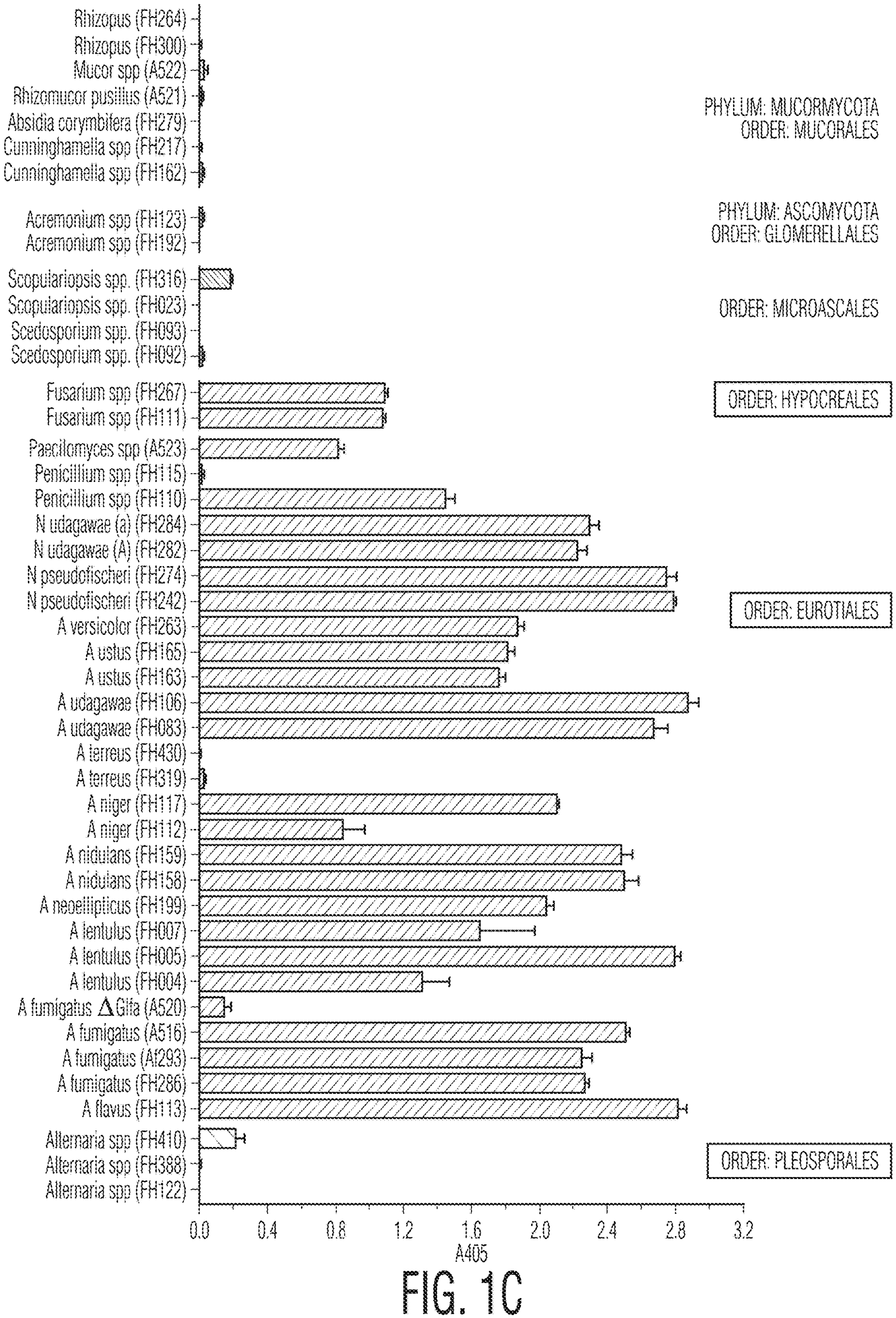
Figure 2:
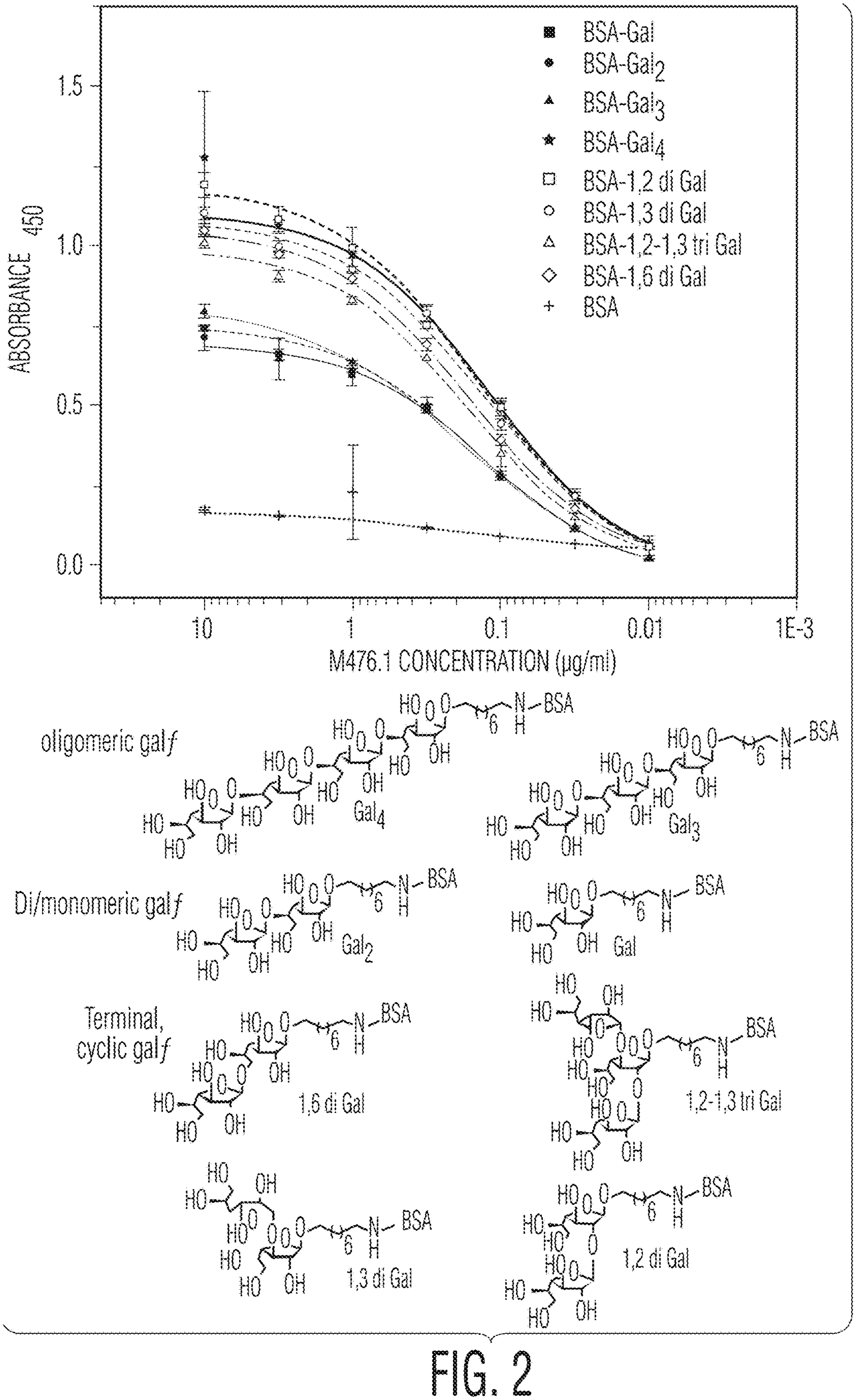
FIG. 2 provides shows mAb476 ELISA to bovine serum albumin (BSA)-glycoconjugates, demonstrating reactivity to long-chain galf and relatively robust reactivity to both dimeric and monomeric galF.
Figure 4A:
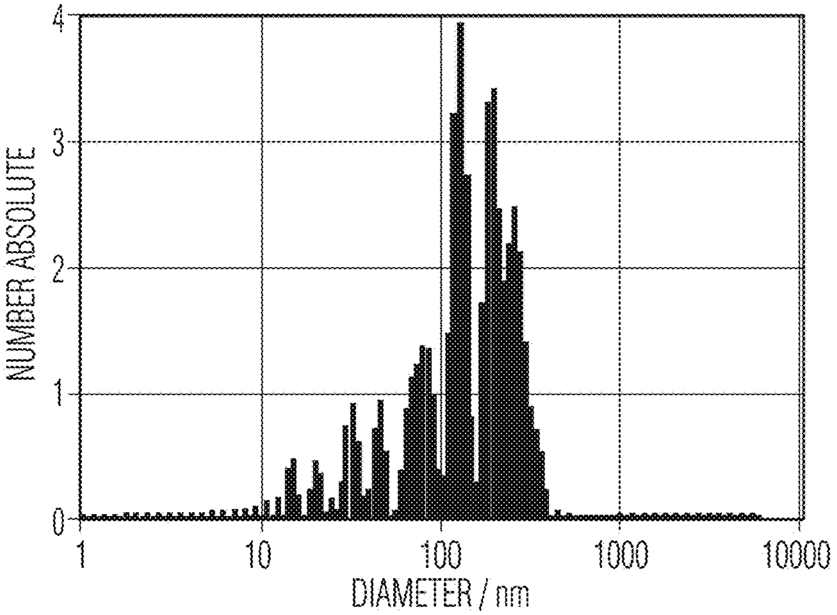
FIGS. 4A-4F demonstrates data showing that *Aspergillus* makes EVs.
Figure 4B:
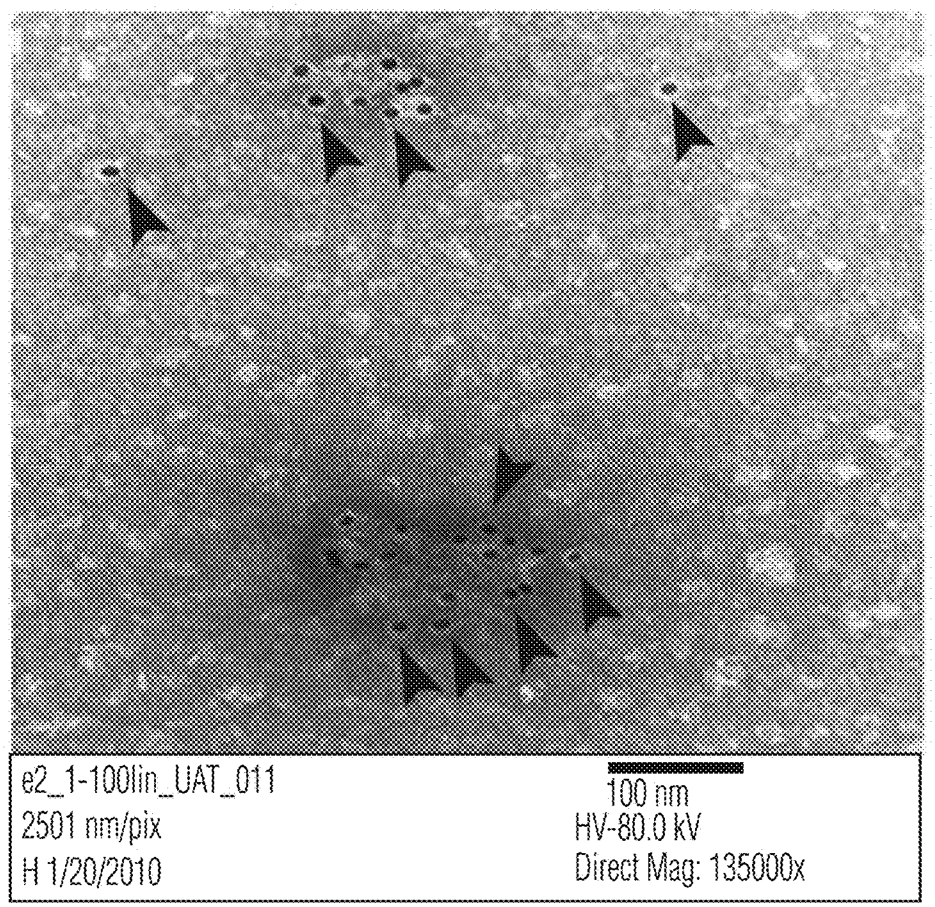
Figure 4C:
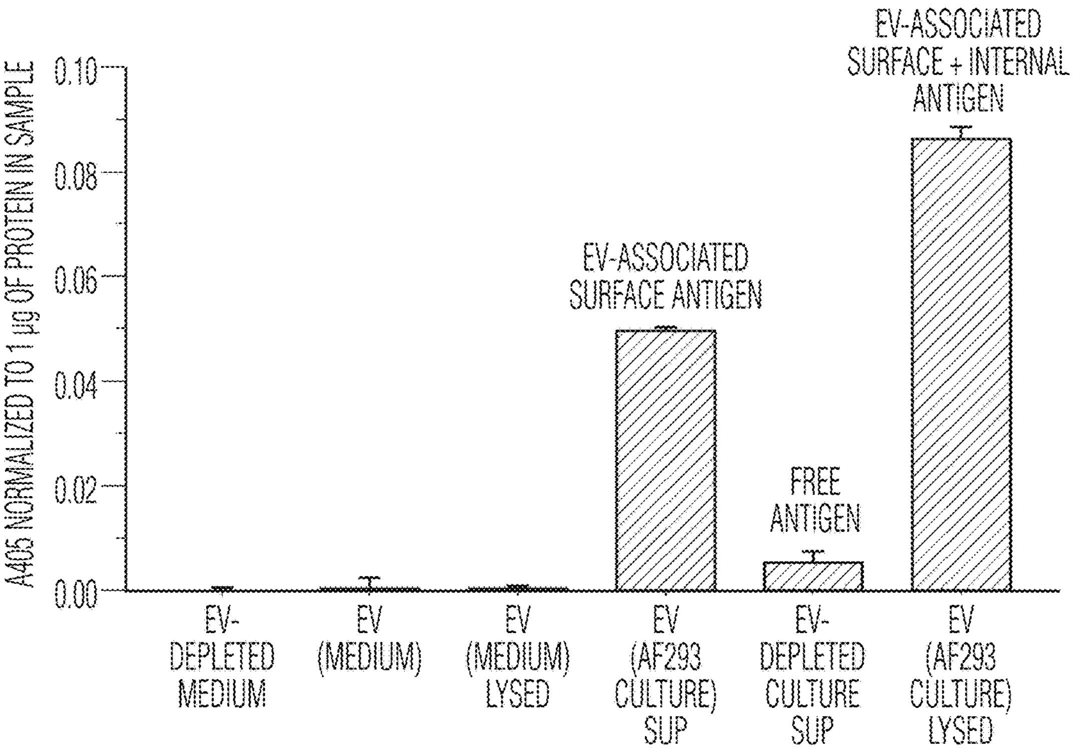
Figure 4D:
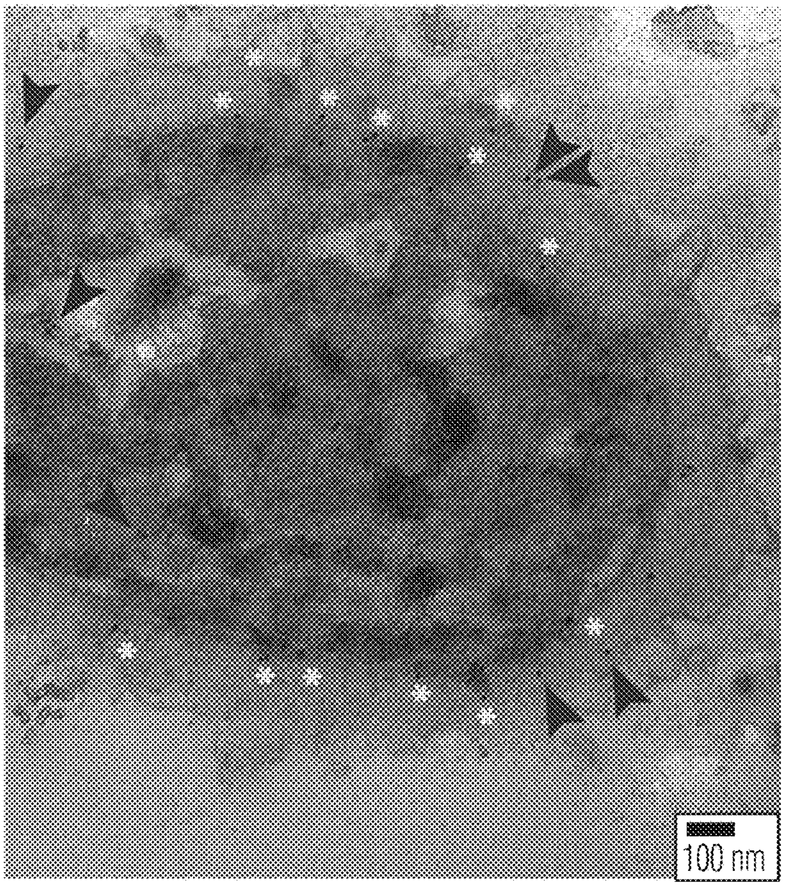
Figure 4E:
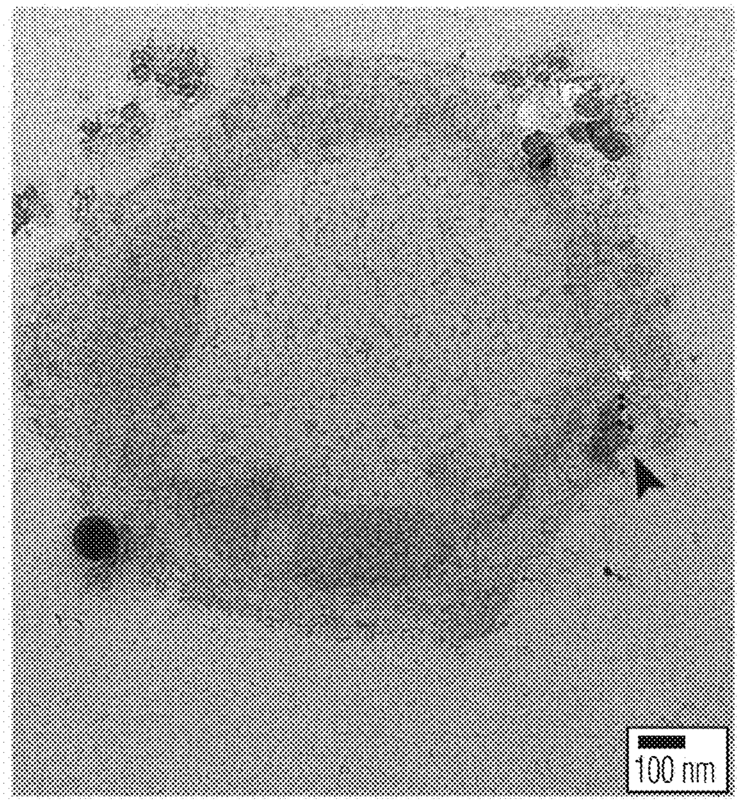
Figure 4F:
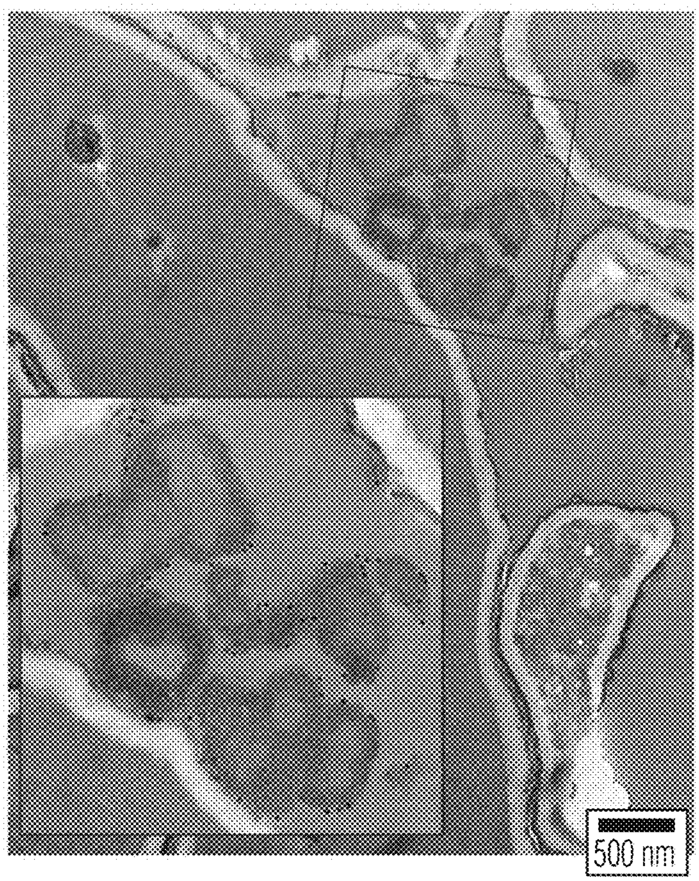
Figure 5A:
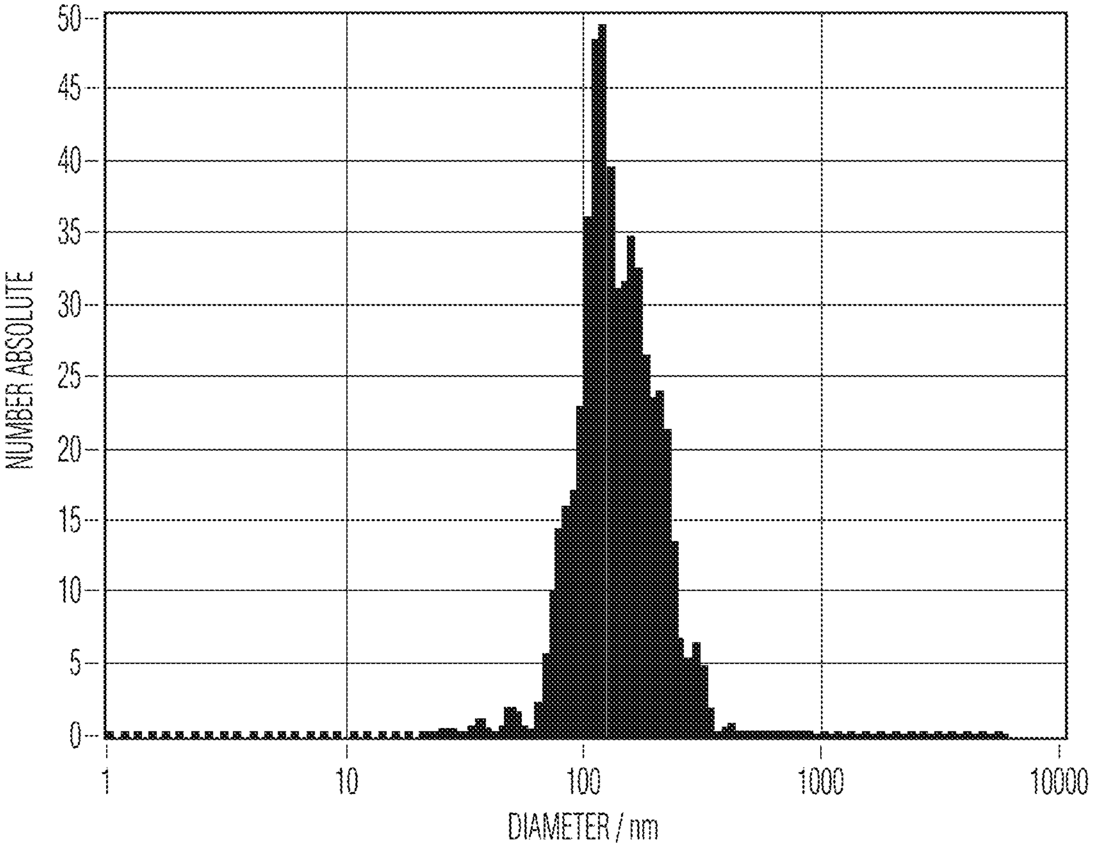
FIGS. 5A-5C shows galF-bearing EVs prominent in IA urines.
Figure 5B:
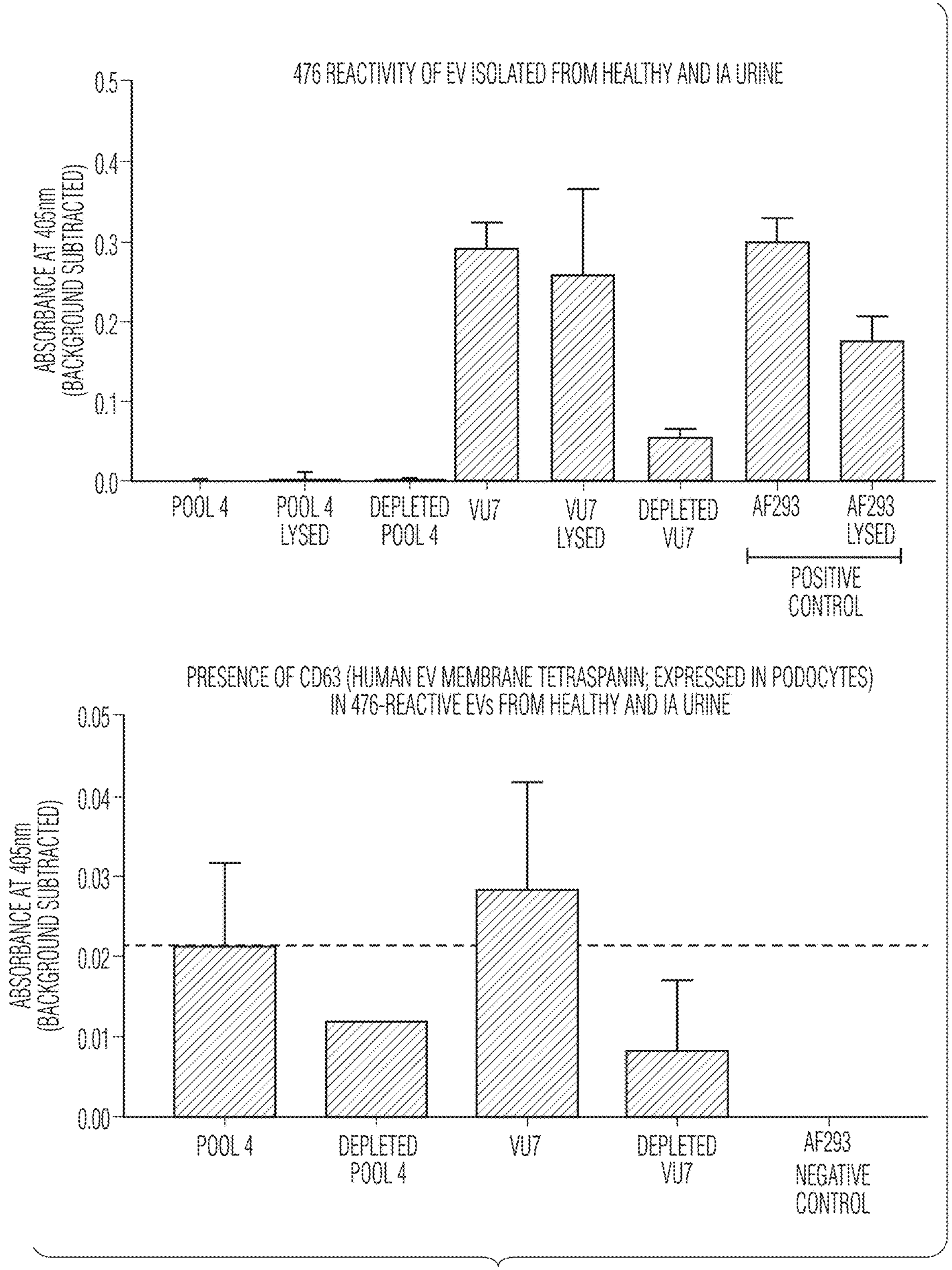
Figure 5C:
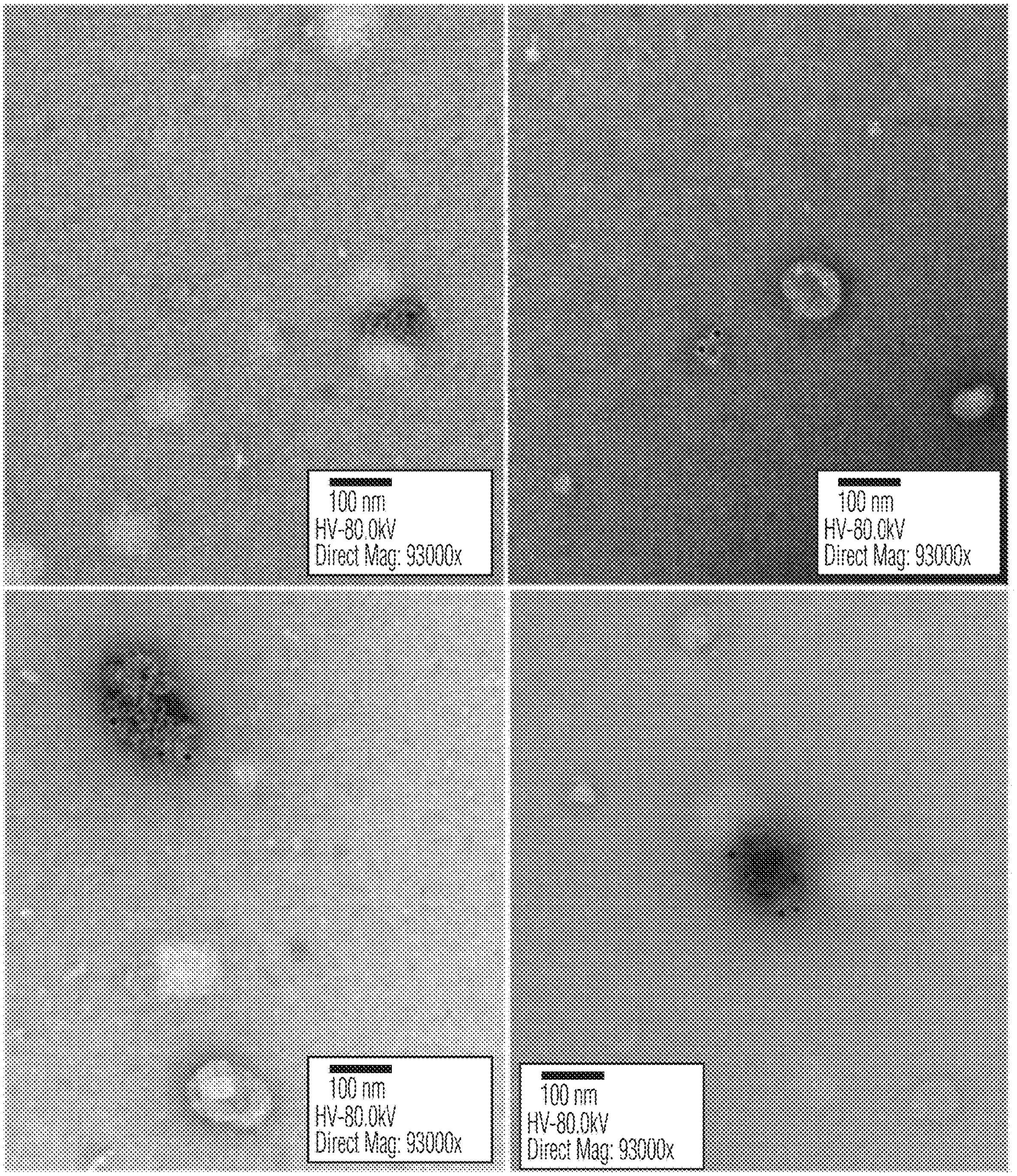
Figure 6:
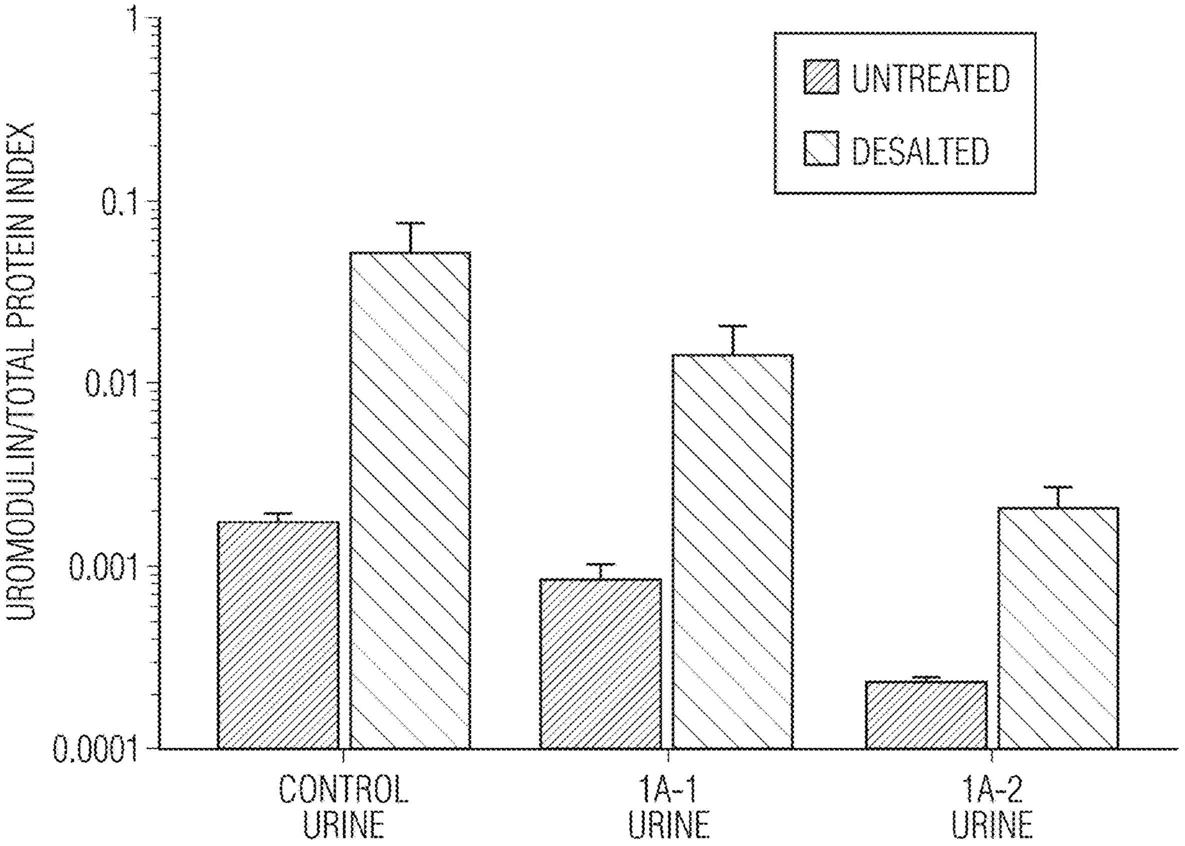
FIG. 6 provides data demonstrating uromodulin levels in urine relative to total protein content. Levels of monomerized uromodulin are shown in urine from controls and people with invasive aspergillosis (IA), with and without processing to remove salts.
Figure 7:
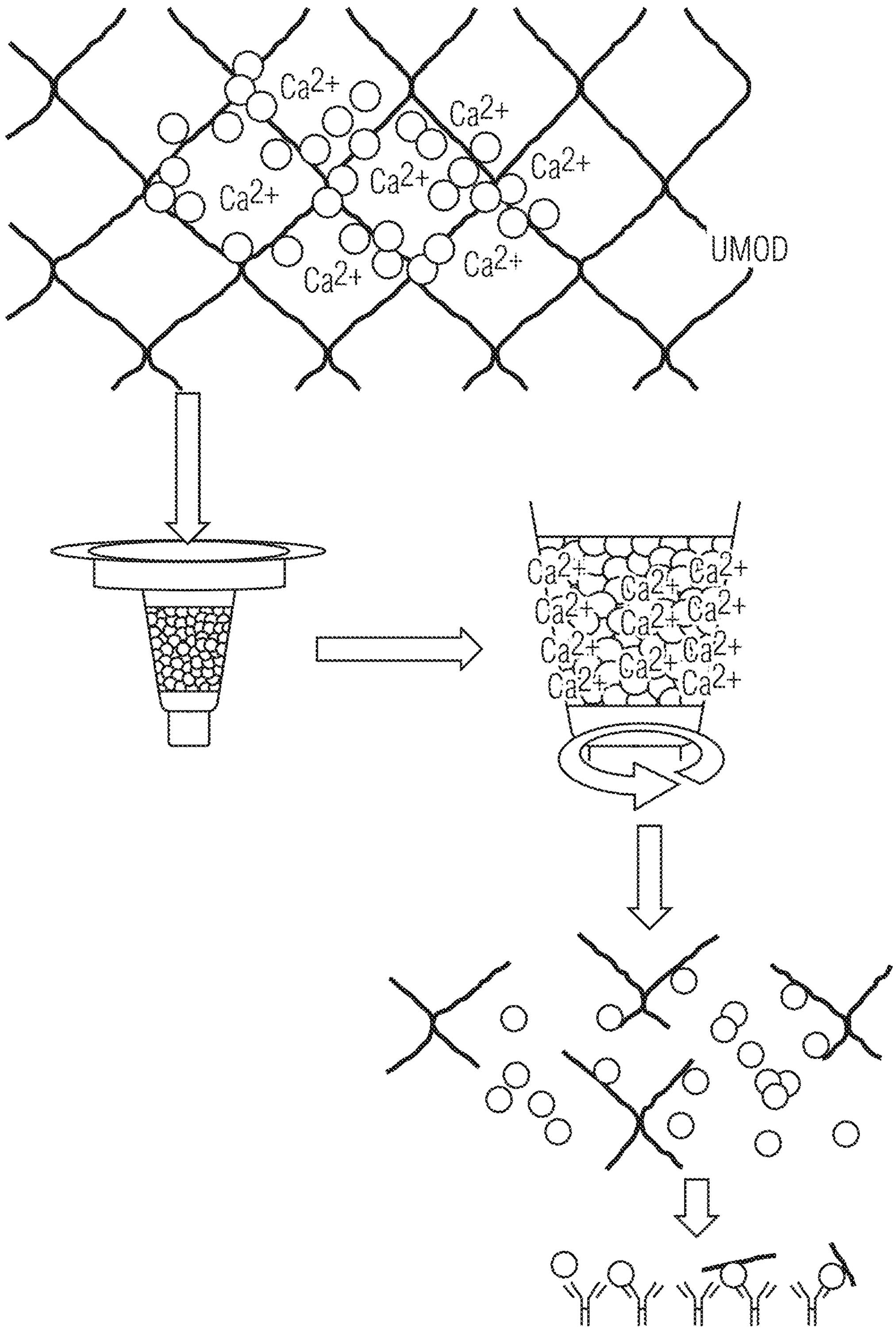
FIG. 7 provides a schematic showing sample processing, i.e. removing calcium, fragments the filamentous uromodulin protein into monomers; these monomers are then able to be centrifuged through the desalting column, enriching the EVs.

The following detailed description is exemplary and explanatory and is intended to provide further explanation of the present disclosure described herein. Other advantages, and novel features will be readily apparent to one of ordinary skill in the art from the following detailed description of the present disclosure. Incorporated by reference for all purposes as if fully set forth herein are the following applications: U.S. Provisional Patent Application No. 61/263,498, U.S. patent application Ser. No. 13/511,264, U.S. Pat. No. 9,915,657, U.S. patent application Ser. No. 15/882,278, U.S. patent application Ser. No. 15/889,845, PCT/US2010/057819, U.S. Provisional Patent Application No. 62/503,492, and PCT/US2018/31888.

Extracellular Vesicles

Extracellular vesicles (EVs) are bilayered membrane vesicles secreted by all cell types, and released in the interstitial space or into circulating bodily fluids, where they can travel long distances until they are up taken by receptor cells (Lee T H et al. Semin Immunopathol. 33:455-467. 2011). Different terminology is used to describe EVs based on their morphology and methods of cellular production. Exosomes, microvesicles, ectosomes, microparticles and others, are classified based on their size, shape and membrane surface composition (Zhang H G et al. Am J Pathol. 184:28-41. 2014). The most accepted classification in the literature shows two major groups of EVs, based on their mechanism of biogenesis and sizes: exosomes and microvesicles (or ectosomes). Additionally, apoptotic bodies have been considered by some as a third category of EVs (Choi D S et al. Proteomics. 13:1554-1571. 2013).

Exosomes are 40-140 nm diameter bilayered-membrane vesicles of endocytic origin, with a cup-shaped morphology, showing densities ranging between 1.13-1.19 g/ml (Van der Pol E, et al. Pharmacol Rev. 64:676-705. 2012.). The exosomes are originated by the inward budding of clathrin-coated domains in the plasma membrane, generating the multivesicular bodies (MVBs) containing intraluminal vesicles (ILVs) in the late endosome. The formation of ILVs occurs during the endosome maturation, when specific cytosolic proteins are incorporated into these vesicles inside de MVBs. These initial steps occur under control of the ESCRT (endosomal sorting complex required for transport) machinery. Later, the MVBs fuse with lysosomes for degradation or with the cell membrane releasing the exosomes to the extracellular space, process regulated by the RAB family (Simpson R J, et al. Proteomics. 8:4083-4099. 2008). Microvesicles (or ectosomes) are larger than exosomes, with size ranging between 100 and 1,000 nm in diameter and heterogeneous in morphology. Differently from the exosomes, microvesicles (MVs) are originated from the plasma membrane through direct outward budding into the extracellular space. During this process, the newly originated vesicle captures the donor cellular cytosolic content and the receptors on the plasma membrane. The regulation of MVs biogenesis is intracellular calcium-dependent and it is the result of the activation of cell surface receptors, phospholipid redistribution and cytoskeletal protein contraction (Principe S. et al. Proteomics. 13:1608-1623. 2013.). The apoptotic bodies (ABs) are membrane vesicles, heterogeneous in shape, showing sizes ranging between 50-500 nm in diameter. The ABs are released from the outward protrusion of the plasma membrane during the late phase of cell death by apoptosis and are featured by the presence of organelles inside the vesicles (Akers J C et al. J Neurooncol. 113:1-11. 2013).

Exosomes can be found in the bodily fluids in a variety of host tissues, especially tumors and many reports have proved that the exosomal content as proteins, mRNA, miRNA and DNA can reflect the disease status, making them suitable for biomarkers for non-invasive diagnostic and prognosis purposes. The inventors herein have further discovered that exosomes, or extracellular vesicles, are produced with certain pathogenic organisms that frequently cause lung infections. In this example, the filamentous fungus *Aspergillus fumigatus* is shown to produce EVs in liquid growth in vitro; in humans with documented aspergillosis, fungal EVs are shown to be rapidly excreted into urine. The inventors have discovered that urine detection of fungal EVs is the basis of a novel urinary diagnostic test.

EV—Associated Proteins and Biological Components

Typically, EVs cannot be precipitated out of solution, except by high-speed ultracentrifugation. In certain scenarios, EVs may be present in biofluid in association with additional biological components such as proteins. One such protein comprises uromodulin (also known as Tamm-Horsfall protein), it is exclusively produced in the kidney and is the most abundant protein in normal urine (Devuyst et al. Nature Reviews Nephrology volume 13, pages 525-544 (2017). Until now, most of the function of uromodulin remained elusive, but the available data suggested that this protein might regulate salt transport, protect against urinary tract infection and kidney stones, and have roles in kidney injury and innate immunity. Interest in uromodulin was boosted by genetic studies that reported involvement of the UMOD gene, which encodes uromodulin, in a spectrum of rare and common kidney diseases. Rare mutations in UMOD cause autosomal dominant tubulointerstitial kidney disease (ADTKD), which leads to chronic kidney disease (CKD). Moreover, genome-wide association studies have identified common variants in UMOD that are strongly associated with risk of CKD and also with hypertension and kidney stones in the general population.

It is known that the filamentous form of uromodulin serves to 'entrap' human EVs in urine, and the uromodulin—EV complexes can be co-precipitated with low-speed centrifugation [Fernandez—Llama Kidney International 77, 736-42 (2010); Kosanovic & Jankovic Biotechniques 57:143-49 (2014)]. The inventors herein discovered that processing urine samples with desalting enables optimization of EV-uromodulin co-precipitation using low-speed rather than high-speed centrifugation, preserving recognition of EV antigens using techniques that include but are not limited to immunodiagnostics for galF-containing EVs.

Current Methods for Diagnosing Microbial Infections in Biological Samples

It has been previously reported that galactomannan, or an antigen that shares a cross-reactive epitope identified by the antibody EBA1/EBA2, is excreted in urine in rabbits and humans infected with *Aspergillus* species. See Klont, R. R., M. A. Mennink-Kersten, and P. E. Verweij, Utility of *Asper-*

*gillus* antigen detection in specimens other than serum specimens. Clin Infect Dis, 2004. 39(10): p. 1467-74; Dupont, B., et al., Galactomannan antigenemia and antigenuria in aspergillosis: studies in patients and experimentally infected rabbits. J Infect Dis, 1987. 155(1): p. 1-11; Bennett, J. E., M. M. Friedman, and B. Dupont, Receptor-mediated clearance of *Aspergillus* galactomannan. J Infect Dis, 1987. 155 (5): p. 1005-10; Rogers, T. R., K. A. Haynes, and R. A. Barnes, Value of antigen detection in predicting invasive pulmonary aspergillosis. Lancet, 1990. 336 (8725): p. 1210-3; Ansorg, R., E. Heintschel von Heinegg, and P. M. Rath, *Aspergillus* antigenuria compared to antigenemia in bone marrow transplant recipients. Eur J Clin Microbiol Infect Dis, 1994. 13 (7): p. 582-9; Salonen, J., et al., *Aspergillus* antigen in serum, urine and bronchoalveolar lavage specimens of neutropenic patients in relation to clinical outcome. Scandinavian Journal of Infectious Diseases, 2000. 32: p 485-490. No diagnostic assay for *Aspergillus* species currently relies on detection of an antigen in urine.

Diseases Caused by *Aspergillus* Species

*Aspergillus* spp. are exogenously acquired into the lungs. The organism grows in a sporulating phase in the environment, in which asexual reproduction yields small, hydrophobic, readily aerosolized, ubiquitous conidia. Disease occurs when conidia that are inhaled into the lungs escape phagocytosis and germinate into angioinvasive hyphae. Clinical manifestations arise both from microbial invasion and from aberrant inflammatory responses, creating a spectrum of allergic, saprophytic, semi-invasive, and invasive manifestations. As the organism might not be circulating in blood at the time of pulmonary disease, especially in non-neutropenic hosts, development of blood-based diagnostics requires a platform that can detect biomarkers without necessitating circulating cells. Fortunately, many fungi, including *Aspergillus* species, secrete polysaccharides or other metabolites during growth, enabling detection of these products prior to actual blood stream invasion. For instance, absorption of the galactoxylomannan (GXM) polysaccharide of *Cryptococcus neoformans* capsules occurs well before the organism is blood-borne; hence, the diagnostic test that relies on detection of this antigen is sensitive and provides 'early' diagnostic results.

Epidemiology and Approach to Fungal Infections

During the 1990's, a marked change occurred in the opportunistic infections that occur in patients with hematologic malignancies and in recipients of HCT, largely because of effective prevention of infection caused by cytomegalovirus (CMV) and *Candida albicans*. Early studies validated the use of ganciclovir administered pre-emptively in the setting of pp65 antigenemia to prevent CMV disease, Boeckh, M., et al., Successful modification of a pp65 antigenemia-based early treatment strategy for prevention of cytomegalovirus disease in allogeneic marrow transplant recipients. Blood, 1999. 93 (5): p. 1781-2; Boeckh, M., T. Gooley, and R. Bowden, Effect of high-dose acyclovir on survival in allogeneic marrow transplant recipients who received ganciclovir at engraftment or for cytomegalovirus pp65 antigenemia. J Infect Dis, 1998. 1998 (178): p. 1153-7; Boeckh, M., et al., Plasma polymerase chain reaction for cytomegalovirus DNA after allogeneic marrow transplantation: comparison with polymerase chain reaction using peripheral blood leukocytes, pp65 antigenemia, and viral culture. Transplantation, 1997. 64: p. 108-113; Boeckh, M., et al., Cytomegalovirus pp65 antigenemia-guided early treatment with ganciclovir versus ganciclovir at engraftment after allogeniec marrow transplantation: a randomized double-blind study. Blood, 1996. 88(10): p. 4063-4071, and the utility of prophylactic fluconazole for preventing candidiasis. Slavin, M. A., et al., Efficacy and safety of fluconazole prophylaxis for fungal infections after marrow transplantation—a prospective, randomized, double-blind study. Journal Of Infectious Diseases., 1995. 171 (6): p. 1545-52. Subsequent independent analyses of transplant outcomes showed that two variables associated with survival after HCT for chronic myelogenous leukemia were receipt of ganciclovir and fluconazole. Hansen, J. A., et al., Bone marrow transplants from unrelated donors for patients with chronic myeloid leukemia. The New England Journal of Medicine, 1998. 338: p. 962-8. These studies demonstrate that prevention of infection is a critical component in improving the overall outcomes of transplant and cancer chemotherapy. Hence, attempts to improve outcomes should be focused not only on establishing methods for early diagnosis, but also on developing methods to enable targeted prevention.

Unfortunately, successful prevention of infection has been limited by the emergence of pathogenic molds, particularly *Aspergillus* species. A review of aspergillosis at the Fred Hutchinson Cancer Research Center (FHCRC) between 1987 and 1993 showed that the incidence of infection increased during the first six months of 1993. More recent studies showed that the overall incidence of infection tripled over the last decade, such that this infection now accounts for 10-20% of deaths in allogeneic HCT recipients. Marr, K., et al., Epidemiology and outcome of mould infections in hematopoietic stem cell transplant recipients. Clin Infect Dis, 2002. 34: p. 909-917; Wald, A., et al., Epidemiology of *Aspergillus* infections in a large cohort of patients undergoing bone marrow transplantation. The Journal of Infectious Diseases, 1997. 175: p. 1459-66.

Reported incidences vary, however, largely due to diagnostic biases and differences in aggressiveness in establishing infection vs. treating presumptively. For example, a recent multicenter study shows that the incidence of aspergillosis in both autologous and allogeneic HCT recipients varies per center, with some centers reporting a very high number of cases, and other centers reporting few to no recognized infections. Neofytos, D., et al., Epidemiology and outcome of invasive fungal infection in adult hematopoietic stem cell transplant recipients: analysis of Multicenter Prospective Antifungal Therapy (PATH) Alliance registry. Clin Infect Dis, 2009. 48 (3): p. 265-73. The majority of cases of aspergillosis occur late after transplant during the non-neutropenic period in association with severe GVHD and corticosteroid use, with a median of approximately 82 days in recipients of allogeneic HCT. Surprisingly, even recipients of autologous grafts now develop IA late after HCT, at a median of 51 days after HCT. The range of days at IA diagnosis is extremely broad; in this most recent multicenter study, IA diagnoses ranged from day 0 to day 6,542 after receipt of stem cells.

Invasive fungal infections caused by other molds occur yet later after allogeneic and autologous HCT. Timing of infection relative to HCT and the increased duration of risk well beyond that of neutropenia complicates development of preventative strategies, as any effective regimen would require either long-term administration of a drug or frequent monitoring in the outpatient setting (or both). The trend to late development of IA also applies to patients at risk for infection by virtue of receipt of solid organ transplantation (SOT). In the same multicenter cohort evaluated for epidemiology and outcomes of IA cited above, which summarized invasive fungal infections in 429 SOT recipients in 17 U.S. centers (PATH alliance), it was documented that IA occurs well beyond discharge after transplantation in liver, lung, and heart transplant recipients, at a median of 100 days (range 10, 146), 504 days (range 3, 417) and 382 days (range 31, 309) after transplantation. Neofytos et al, Epidemiology and outcome of invasive fungal infections in solid organ transplant recipients. Transpl Infect Dis, 2010. 12 (3): p. 220-9. Hence, results of recent single-center and multi-center epidemiology studies demonstrate that fungal infections, especially those caused by *Aspergillus* species, typically occur late after immunosuppressive procedures, such as transplant, and with unpredictable timing. Accordingly, establishing methods to prevent advanced disease and to diagnose IA early will require more than optimization of assay performance parameters, but also will require a strategy, such as POC testing, that can be employed effectively in an outpatient setting.

Diagnosis of Pathogenic Fungal Infections: An Overview

Invasive fungal infections are notoriously difficult to diagnose, in part because the organisms are difficult to cultivate in the laboratory. This difficulty is secondary to multiple factors, including growth of the organism in morphologies that do not replicate by simple binary fission, and requirements for alternative growth conditions in the laboratory. Also, it can be difficult to obtain adequate tissue samples from the most frequently involved site, i.e., the lungs, without inducing excessive morbidity. Adjunctive diagnostic tests have been developed and are in common use, however, for multiple fungal infections, including cryptococcosis and infections caused by multiple endemic fungi (e.g., histoplasmosis and coccidiomycosis), which are frequently diagnosed by using immunoassays that detect fungal polysaccharide antigens in blood, urine, or other fluids, such as cerebral spinal fluid. For example, new tests that detect *Histoplasma, Blastomyces*, and *Coccidioides* galactomannans in urine have been developed and appear to have utility in early diagnosis of disease. Durkin, M., et al., Diagnosis of coccidioidomycosis with use of the *Coccidioides* antigen enzyme immunoassay. Clin Infect Dis, 2008. 47 (8): p. e69-73; Spector, D., et al., Antigen and antibody testing for the diagnosis of blastomycosis in dogs. J Vet Intern Med, 2008. 22 (4): p. 839-43. The form of the antigen, specifically whether the antigen is excreted into urine in free polysaccharide or associated with EVs, remain unknown for infections other than Aspergilloses.

It is not a coincidence that the most successful adjunctive assays in use today detect fungal polysaccharides, as these organisms characteristically have large, complex polysaccharide-rich cell walls that serve both to present antigens and to complicate detection of intracellular components. In some organisms, such as *Cryptococcus* species, polysaccharides associated with the cellular capsule (e.g., glucuronoxylomannan) are released and absorbed in vivo, facilitating detection in peripheral compartments.

Development of successful diagnostic tests that detect nucleic acids, which has been more successfully employed for viral infections, has been more elusive for fungi despite worldwide efforts. In part, this difficulty is due to the complexities of harvesting nucleic acids from fungal cells, presence of multiple genomes within multicellular filamentous organisms, and unreliable 'release' of nucleic acids from local compartments (lung) into systemic circulation.

Current Methods to Diagnose Aspergillosis

Therapeutic advances for aspergillosis have been limited, in part because diagnoses of aspergillosis often are not established until development of radiographic abnormalities, which usually occurs late in the development of an infection given the nonspecific nature of clinical symptoms. Prevention of aspergillosis now constitutes one of the largest critical needs for supportive care. Establishment of successful prevention and therapeutic strategies is contingent on developing better methods to guide therapy.

Multiple platforms exist to detect circulating fungal elements, with most platforms relying on detection of polysaccharide antigens or nucleic acids. Performance of the GM EIA and GL tests is good, but variable, and each test has its own strength and limitation when applied to both serum and bronchoalveolar lavage (BAL). Studies have focused on optimizing assay performance as an aid to diagnosis. No studies, however, have attempted to develop these technologies into platforms more amenable to point-of-care testing. Given the increased incidence of IA occurring outside of the hospital, point-of-care testing is essential to detect early disease.

Current methods for diagnosing IA rely on radiographic detection of "suggestive" abnormalities. Early in the course of IA, the most frequent abnormal findings are nodular lesions, which may, or may not, be surrounded by a hypodense "halo" corresponding to local hemorrhage inflicted by angioinvasive hyphae. Kim, Y., et al., Halo sign on high resolution CT: findings in spectrum of pulmonary diseases with pathologic correlation. J Comput Assist Tomogr, 1999. 23 (4): p. 622-6. As the lesion progresses in a host that has some degree of coordinated immune response, the lesion will cavitate, creating the "air-crescent" sign. Unfortunately, these radiographic abnormalities occur relatively late in the development of disease. Although one study documented that screening with CT scans might allow for earlier diagnoses, Caillot, D., et al., Improved management of invasive aspergillosis in neutropenic patients using early thoracic computed tomographic scan and surgery. Journal of Clinical Oncology, 1997. 15 (1): p. 139-147, routine CT's are costly and not a feasible option for the entire period of time during which patients are at risk, for example after they are discharged from a health care facility and are at home.

Other problems with current diagnostic methods are the insensitivity of tissue culture for filamentous fungi and adverse events inflicted by invasive procedures. The microbiologic yield of bronchoalveolar lavage (BAL) approximates only 60% and depends on the nature of the radiographic lesion and the expertise of the microbiology laboratory. Levy, H., et al., The value of bronchoalveolar lavage and bronchial washings in the diagnosis of invasive pulmonary aspergillosis. Respir Med, 1992. 86 (3): p. 243-8. A review of 214 patients who developed IA after receiving HCT in one center found that only 77% of cases were recognized pre-mortem. Wald, A., et al., Epidemiology of *Aspergillus* infections in a large cohort of patients undergoing bone marrow transplantation. The Journal of Infectious Diseases, 1997. 175: p. 1459-66. The histopathologic and microbiologic yield of biopsies achieved with an open procedure or percutaneously is variable and also results in frequent bleeding complications, especially in children. Hoffer, F. A., et al., Accuracy of percutaneous lung biopsy for invasive pulmonary aspergillosis. Pediatr Radiol, 2001. 31 (3): p. 144-52.

In summary, new methods are required to meet two clinical needs: (1) to develop sensitive tests that can be used for screening to detect infection early, thereby allowing for effective preventative algorithms; and (2) to increase the sensitivity of detection of fungi when used in adjunct with standard histopathologic and microbiologic techniques (as an aid to diagnosis). The two primary methods that have been explored for these indications rely on detection of fungal antigen(s) or nucleic acids using immunoassays or polymerase chain reaction (PCR), respectively.

In an embodiment, methods are provided herein for detecting a biological or chemical entity in a sample, wherein the biological or chemical entity is associated with extracellular vesicles, comprising a) processing the sample, (b) using a detection assay to detect the presence of extracellular vesicles and to isolate the extracellular vesicles, (c) processing the extracellular vesicles to expose or release the biological or chemical entity, and (e) detecting the biological or chemical entity released from the extracellular vesicle. In certain embodiments, the extracellular vesicles bind to proteins, glycoproteins, peptides, lipids, nucleic acids or other cellular components. The proteins may comprise uromodulin and fragments thereof. In an embodiment uromodulin may bind to the outside of an extracellular vesicle.

As contemplated herein, processing the sample may comprise passing the sample through a desalting column, passing the sample through a high performance liquid chromatography column, ethanol precipitation, centrifugation, filtration, separation based on size, separation based on charge, filtration based on morphology, microfluidic processing to separate based on size and flow, performing immunomagnetic isolation, precipitation, immunoprecipitation, enzymatic degradation, coagulation, sterilization, incubation, or lysis.

Processing the extracellular vesicles to expose or release the biological or chemical entity may comprise lysis by detergent and detecting the biological or chemical entity may comprise the use of an immunoassay. In general, immunoassays assays contemplated for use herein may comprise detecting the presence of at least one antibody-antigen complex, wherein the detection of the presence of at least one antibody-antigen complex is diagnostic of the presence of a microbe in the sample. As used herein, the term antigen is intended to encompass any protein, glycoprotein or fragment thereof that is capable of generating an antigenic response.

In certain embodiments, the sample is obtained from a source selected from the group consisting of bacteria, viruses, fungi, mycobacteria, protozoa, molds, yeasts, plants, humans, non-humans, multi-cellular parasite, animals, and archeabacteria. The sample may be obtained from a human source. The sample may also be obtained from a source selected from the group consisting of: urine, tissue, blood, serum, plasma, sputum, bronchoalveolar lavage fluid, saliva, tear, vaginal secretion, umbilical cord blood, chorionic villi, amniotic fluid, embryonic tissue, lymph fluid, cerebrospinal fluid, mucosa secretion, peritoneal fluid, ascitic fluid, fecal matter, and body exudates. In certain embodiments, the biological or chemical entity may be from a species different from the species from which the sample was taken. In certain embodiments, the different species may be from a group consisting of fungi, bacteria, viruses, mycobacteria, protozoa, molds, yeasts, plants, humans, non-humans, multi-cellular parasite, animals, and archeabacteria.

In certain embodiments, the fungus is a drug-sensitive fungus or a drug-resistant fungus. As contemplated herein, fungus may comprise: *Aspergillus* species., *Aspergillus fumigatus, Aspergillus flavus, Aspergillus niger, Aspergillus nidulans, Aspergillus terreus, Aspergillus sydowi, Aspergillus flavus, Aspergillus glaucus, Candida species, Candida albicans, Candida tropicalis, Candida parapsilosis, Candida stellatoidea, Candida krusei, Candida parakrusei, Candida lusitanae, Candida tropicalis, Candida guilliermondi, Candida glabrata, Cryptococcus species, Histoplasma species, Coccidioides species, Paracoccidioides species, Blastomyces* species, *Basidiobolus* species, *Conidiobolus* species, *Zygomycetes, Rhizopus* species, *Rhizomucor* species, *Mucor* species, *Absidia* species, *Mortierella* species, *Cunninghamella* species, *Saksenaea* species, *Pseudallescheria* species, *Scedosporium* species, *Alternaria* species, *Sporotrichosis, Fusarium* species, *Trichophyton* species, *Microsporum* species, *Epidennophyton* species, *Scytalidium* species, *Malassezia* species, *Actinomycetes, Sporothrix, Penicillium* species, *Saccharomyces* and *Pneumocystis.*

In certain embodiments, the parasite is a drug-sensitive parasite or a drug-resistant parasite. The parasite may comprise *Leishmania* species, *Leishmanis donovanii, Plasmodium* species, *Plasmodium vivax, Plasmodium ovale, Plasmodium falciparum, Plasmodium malariae, Plasmodium knowlesi, Trypanosoma* species, *Trypanasoma cruzi, Strongyloides species, Toxoplasma species, Toxoplasma gondii, Helminths, Agamococcidiorida,* (*Gemmocystis, Rhytidocystis*), *Eucoccidiorida, Ixorheoridaor Protococcidiorida.*

In an embodiment, the bacteria is a drug-sensitive bacteria a drug-resistant bacteria. As contemplated herein, the bacteria may be selected from the group consisting of: Acidaminococcus, *Acinetobacter, Acinetobacter* Iwoffi, *Aeromonas, Alcaligenes, Bacteroides, Bordetella, Branhamella, Brucella, Calyrnmatobacterium, Campylobacter, Cardiobacterium, Chromobacterium, Citrobacter, Citrobacter freundii, Cotiform group, Edwardsiella, Enterobacter, Enterobacter sakazaki, Enterobacter aerogenes, Enterobacter cloacae, Enterobacter agglomerans, Enterococcus, Enterococcus faecalis, Enterococcus faecium, Escherichia, Escherichia coli, Escherichia coli*-O157, *Flavobacterium, Francisella, Fusobacterium, Haemophilus, Hafnia alvei, Klebsiella, Klebsiella oxytoca, Klebsiella pneumoniae, Legionella, Moraxella, Morganella, Morganella morganii, Neisseria, Pasteurella, Plesiomonas, Proteus, Providencia, Proteus mirabilis, Pseudomonas, Pseudomonas aeruginosa, Salmonella, Salmonella typhimurium, Serratia, Serratia marcescens, Shigella, Shigella flexneri, Streptobacillus, Veillonella, Vibrio, Vibrio cholera, Yersinia, Yersinia enterolitica, Xanthomanas maltophilia, Staphylococcus, Staphylococcus albus, Staphylococcus epidermiditis, Staphylococcus lugdenensis, Staphylococcus aureus, Streptococcus, Streptococcus pneumoniae, Streptococcus dysgalacticae, Micrococcus, Peptococcus, Peptostreptococcus, Bacillus, Bacillus cereus, Clostridium, Lactobacillus, Listeria, Listeria monocytogenes, Erysipelothrix, Propionibacterium, Eubacterium*, and *Corynebacterium.*

In certain embodiments, the virus detected using the methods claimed herein comprise is a DNA virus or an RNA virus. The virus may be selected from the group consisting of: retrovirus, pathogenic virus, non-pathogenic virus, drug-resistant virus, drug-sensitive virus, adeno-associated virus, bird flu virus, cauliflower mosaic virus, cytomegalovirus (CMV), dengue virus, Epstein-Barr virus, feline leukemia virus, flavivirus, *haemophilus* influenza, hemorrhagic fever viruses, hepatitis virus including hepatitis A, B, C, and B, viruses, herpes simplex virus, human herpesvirus type A and B, human immunodeficiency virus (HIV), human papilloma virus, human T-cell lymphotrophic virus, HTLV Type I, HTLV Type II, influenza virus, Japanese encephalitis virus, *Moraxella catarrhalis*, non-typeable *haemophilus*, reovirus, parainfluenza, parvovirus, papova virus, Respiratory syncytial virus, Rubella virus, rotavirus, SARS, tomato bushy stunt virus, varicella-zoster virus, and vaccinia virus.

In an embodiment, the biological or chemical entity detected according to the methods described herein may comprise a biomarker for a disease or disorder. The disease or disorder may comprise cancer, cardiovascular disease, respiratory disease, cerebrovascular disease, Alzheimer's disease, diabetes, influenza, pneumonia, nephritis, or cirrhosis. In certain embodiments, cancer may comprise: carcinoma of the bladder, breast, bronchial, colon, kidney, liver, lung, esophagus, gall-bladder, ovary, pancreas, stomach, cervix, thyroid, prostate, and skin; small cell lung cancer, squamous cell carcinoma, hematopoietic tumors of lymphoid lineage, leukemia, acute lymphocytic leukemia, acute lymphoblastic leukemia, B-cell lymphoma, T-cell-lymphoma, Hodgkin's lymphoma, non-Hodgkin's lymphoma, hairy cell lymphoma, Burkett's lymphoma, hematopoietic tumors of myeloid lineage, acute and chronic myelogenous leukemias, myelodysplastic syndrome and promyelocytic leukemia, tumors of mesenchymal origin, fibrosarcoma and rhabdomyosarcoma, tumors of the central and peripheral nervous system, astrocytoma, neuroblastoma, glioma and schwannomas, melanoma, seminoma, teratocarcinoma, osteosarcoma, xenoderoma pigmentosum, keratoctanthoma, thyroid follicular cancer and Kaposi's sarcoma.

In an embodiment, the novel methods described herein comprise (a) processing a sample to decrease/minimize/reduce human intelectin (hIntL) binding of microbial antigens including galactofuranose residues present in the sample; (b) using a detection assay to detect the presence of extracellular vesicles and to isolate the extracellular vesicles, (c) processing the extracellular vesicles to expose or release the biological or chemical entity, (d) contacting the treated sample with at least one antibody specific for at least one, antigen, polysaccharide or glycoprotein comprising a galactofuranose residue in an effective amount to produce a detectable amount of antibody-antigen complex; and (e) detecting the presence of at least one antibody-antigen complex, wherein the detection of the presence of at least one antibody-antigen complex is diagnostic of the presence of microbial extracellular vesicles in the sample. The method may comprise treating the sample by contacting the sample with a substrate, wherein the substrate comprises an intelectin-binding component. In certain embodiments, the intelectin-binding component comprises glycerol, 3-Keto-2-deoxyoctonic acid; D-glycerol-1-phosphate, D-mannoheptose, sepharose, or sepharose-containing particles (i.e. latex, polystyrene or glass beads, microspheres or gels). The antibody may comprise mAb476, and the sample may comprise urine. The detection of the presence of an antibody-antigen complex may be diagnostic for the presence of *Aspergillus* in the body.

Provided herein are methods for detecting fungal antigens in a urine sample, wherein the fungal antigens are associated with extracellular vesicles, comprising: processing the sample using a desalting column, using a detection assay to detect the presence of extracellular vesicles and to isolate the extracellular vesicles, processing the extracellular vesicles to expose or release the fungal antigens, and detecting the fungal antigens released from the extracellular vesicle. The extracellular vesicles may be bound to uromodulin and the sample may be processed by passing it through a desalting column comprising a substrate for binding an intelectin-binding component. In an embodiment, processing of the sample, such as by desalting results in the breaking apart of uromodulin, allowing precipitation and/or centrifugation. The fungal antigens may be released from the extracellular vesicle by contacting the treated sample with at least one antibody specific for at least one polysaccharide comprising a galactofuranose residue in an effective amount to produce a detectable amount of antibody-polysaccharide complex; and detecting the presence of at least one antibody-polysaccharide complex, wherein the detection of the presence of at least one antibody-polysaccharide complex is diagnostic of the presence of a microbe in the sample. The antibody may comprises mAb476. Detection of the presence of an antibody-polysaccharide complex is diagnostic of the presence of *Aspergillus* in the sample.

Point-of-Care Diagnostics Such as Lateral Flow Devices and Dipstick Assays

The ability to provide test results rapidly to the patient and/or healthcare provider is very important to impact outcomes of multiple conditions. Rapid tests to aid diagnosis and enable early detection of multiple diseases and physiologic conditions are being developed. Such tests are especially useful when they can be applied with self-testing and require little in the way of laboratory processing. Examples of point-of-care (POC) test devices in common use today include pregnancy and fertility tests, as well as assays to follow blood glucose in diabetics. Development of diagnostic tests for infections that use POC testing are especially important in resource-poor settings; for this reason, POC testing has become a new goal to be achieved for infections such as HIV, malaria, and hepatitis. Similarly, POC testing has the potential of impacting clinical outcomes when applied to infections that occur in the outpatient setting, not only by providing indications of disease, but by enabling development of more robust prevention algorithms.

Commonly used immunoassays in diagnostic and research use include radio-immunoassays and enzyme-linked immunosorbent assays (ELISAs). Many of these elaborately configured immunoassays use monoclonal antibodies (mAbs) that possess the ability to bind specifically to the analyte being tested, thereby enhancing the accuracy of the assay. Various approaches have been described for carrying out enzyme immunoassays. A considerable number of these approaches, starting with the earliest of ELISAs, are solid-phase immunoassays in which the analyte to be detected is bound to a solid matrix directly (Direct ELISA) or indirectly (Sandwich ELISA), in which the analyte is captured on a primary reagent. The choice of the solid matrix depends on procedural considerations. A common matrix is the polystyrene surface of multi-well microtiter plates.

These types of assays also are amenable to developing POC devices, in which systems can be self-contained so that output is readable by the user. This characteristic is especially useful when collection of a sample to be tested does not require medical intervention (e.g., urine, saliva, or sputum). One device that enables this is the lateral-flow device (LFD). These devices use a multi-layered construction containing both absorbent and non-absorbent components to form a solid-phase. The capture and/or recognition reagents (antigen or antibody) are pre-applied to specific areas within the assembled apparatus and the analyte is allowed to flow through the system to come into contact with reagents. Often, for the purpose of self-containment, the reagent components are added in a dried state so that fluid from the sample re-hydrates and activates them. Conventional ELISA techniques can then be used to detect the analyte in the antigen-antibody complex. In some embodiments, the system can be designed to provide a colorimetric reading for visual estimation of a binary response ('yes' or 'no'), or it can be configured to be quantitative.

Lateral flow devices are used to detect analytes in multiple body fluids, including serum and urine. To date, these types of devices have seen the most use for detecting circulating endogenous analytes; perhaps the most common use of this type of device is in the ubiquitous POC pregnancy test. Current efforts are being directed toward detecting microbial analytes, including nucleic acids, in the setting of viral infections (e.g., influenza, respiratory syncytial virus, and the like), Nielsen, K., et al., Prototype single step lateral flow technology for detection of avian influenza virus and chicken antibody to avian influenza virus. J Immunoassay Immunochem, 2007. 28 (4): p. 307-18; Mokkapati, V. K., et al., Evaluation of UPlink-RSV: prototype rapid antigen test for detection of respiratory syncytial virus infection. Ann N Y Acad Sci, 2007. 1098: p. 476-85; bacterial infections (e.g., *S. pneumoniae, Legionella*, Mycobacteria), Koide, M., et al., Comparative evaluation of Duopath *Legionella* lateral flow assay against the conventional culture method using *Legionella pneumophila* and *Legionella* anisa strains. Jpn J Infect Dis, 2007. 60 (4): p. 214-6.

One assay that is in use worldwide is the BinaxNOW pneumococcal urinary antigen test; this assay evolved after the serum-based platform was shown to be effective, but cumbersome. The urinary POC device can be particularly useful when employed in high-risk patients as a POC testing device. Roson, B., et al., Contribution of a urinary antigen assay (Binax NOW) to the early diagnosis of pneumococcal pneumonia. Clin Infect Dis, 2004. 38 (2): p. 222-6; Weatherall, C., R. Paoloni, and T. Gottlieb, Point-of-care urinary pneumococcal antigen test in the emergency department for community acquired pneumonia. Emerg Med J, 2008. 25 (3): p. 144-8. This issue is particularly relevant in the context of the presently disclosed subject matter, as the polysaccharides in the pneumococcus capsule have some structural similarity to those of *Aspergillus*. Kappe, R. and A. Schulze-Berge, New cause for false-positive results with the Pastorex *Aspergillus* antigen latex agglutination test. J Clin Microbiol, 1993. 31 (9): p. 2489-90; Stynen, D., et al., Rat monoclonal antibodies against *Aspergillus* galactomannan. Infect Immun, 1992. 60 (6): p. 2237-45; Swanink, C. M., et al., Specificity of a sandwich enzyme-linked immunosorbent assay for detecting *Aspergillus* galactomannan. J Clin Microbiol, 1997. 35 (1): p. 257-60.

Lateral Flow Device and Optimized Methods of Use Thereof for Diagnosing Microbial Infections Preliminary studies have demonstrated that polysaccharide antigens of *A. fumigatus* (e.g., galF) are renally concentrated in animal model and are excreted in urine such that the sensitivity and specificity of a urine-based assay may equal or exceed that of serum based testing. Urinary detection of antigens would enable development of an easy-to-use POC testing method that would enable frequent testing in the outpatient setting, thus aiding the ability to diagnose and optimize screening strategies employed to detect infection early in the course of disease. Accordingly, in some embodiments, the presently disclosed subject matter provides a POC test to detect *Aspergillus* galF-containing antigens in urine. Monoclonal antibodies that recognize galactofuranose residues of *A. fumigatus* galF have been developed and are used in the presently disclosed galF test.

A standard ELISA format was used as a screen to identify antibodies to use for capture on the immobilized device. The identified antibody can be used as a capture antibody with point of care testing device (strip), which can be optimized for conditions to detect galF-antigen (antibody concentration, incubation conditions, and the like).

The term "dipstick assay" as used herein means any assay using a dipstick in which sample solution is contacted with the dipstick to cause sample solution to move by capillary action to a capture zone of the dipstick thereby allowing a target antigen in the sample solution to be captured and detected at the capture zone. To test for the presence of analyte, the contact end of the dipstick is contacted with the test solution. If analyte is present in the test solution it travels to the capture zone of the dipstick by capillary action where it is captured by the capture antibody. The presence of analyte at the capture zone of the dipstick is detected by a further anti-analyte antibody (the detection antibody) labelled with, for example, colloidal gold.

These dipstick tests have several advantages. They are easy and cheap to perform, no specialist instruments are required, and the results are obtained rapidly and can be read visually. These tests are, therefore, particularly suited for use in a physician's office, at home, in remote areas, and in developing countries where specialist equipment may not be available. They can be used, for example, to test whether a patient is infected with a disease causing micro-organism such as *A. fumigatus*.

To perform a method of the first aspect of the invention, the targeting agent and labels may simply be added to the test solution and the test solution then contacted with the contact end of the chromatographic strip. Such methods are easier to perform than the method disclosed in WO 00/25135 in which two separate wicking steps are required. The results may, therefore, be obtained more rapidly, and yet the sensitivity of analyte detection is higher.

The term "chromatographic strip" is used herein to mean any porous strip of material capable of transporting a solution by capillarity. The chromatographic strip may be capable of bibulous or non-bibulous lateral flow, but preferably bibulous lateral flow. By the term "non-bibulous lateral flow" is meant liquid flow in which all of the dissolved or dispersed components of the liquid are carried at substantially equal rates and with relatively unimpaired flow laterally through the membrane as opposed to preferential retention of one or more components as would occur with "bibulous lateral flow." Materials capable of bibulous lateral flow include paper, nitrocellulose, and nylon. A preferred example is nitrocellulose.

The labels may be bound to the ligands of the targeting agent by pre-mixing the targeting agent with the labels before the targeting agent is added to (or otherwise contacted with) the test solution. However, in some circumstances, it is preferred that the targeting agent and labels are not pre-mixed because such pre-mixing can cause the targeting agent and labels to precipitate. Thus, the targeting agent and the labels may be added separately to (or contacted separately with) the test solution. The targeting agent and the labels can be added to (or contacted with) the test solution at substantially the same time, or in any order.

The test solution may be pre-incubated with the targeting agent and labels before the test solution is contacted with the contact end of the chromatographic strip to ensure complex formation. The optimal time of pre-incubation will depend on the ratio of the reagents and the flow rate of the chromatographic strip. In some cases, pre-incubation for too long can decrease the detection signal obtained, and even lead to false positive detection signals. Thus, it may be necessary to optimize the pre-incubation time for the particular conditions used.

It may be desired to pre-incubate the targeting agent with the test solution before binding the labels to the targeting agent so that the targeting agent can be allowed to bind to analyte in the test solution under optimum binding conditions. Generally, the presently disclosed subject matter provides a method for diagnosing a microbial infection in a biological sample from a mammalian subject suspected of having, having, or susceptible to having a microbial infection, by detecting the presence of at least one polysaccharide comprising a galF residue in a biological sample of the mammalian subject, the method comprising: (a) treating the biological sample to decrease or minimize human intelectin-1 (hIntL-1) binding of galF residues present in the sample; (b) contacting the treated sample of (a) with at least one antibody specific for at least one polysaccharide comprising a galF residue in an effective amount to produce a detectable amount of antibody-polysaccharide complex; and (c) detecting the presence of at least one antibody-polysaccharide complex, wherein the detection of the presence of at least one antibody-polysaccharide complex is diagnostic of a microbial infection in a mammalian subject.

In accordance with another embodiment, the present invention provides a method for diagnosing a microbial infection in a biological sample from a mammalian subject suspected of having, having, or susceptible to having a microbial infection by detecting the presence of at least one polysaccharide comprising a galF residue in a biological sample of the mammalian subject, the method comprising: (a) treating the biological sample comprising contacting the sample with a substrate such as a ligand which binds directly to intelectin, or calcium or mono and divalent cations with high affinity, to inhibit human intelectin (hIntL) binding of galF residues present in the sample; (b) contacting the treated sample of (a) with at least one antibody specific for at least one polysaccharide comprising a galF residue in an effective amount to produce a detectable amount of antibody-polysaccharide complex; and (c) detecting the presence of at least one antibody-polysaccharide complex, wherein the detection of the presence of at least one antibody-polysaccharide complex is diagnostic of a microbial infection in a mammalian subject.

The microbial infection can be selected from the group consisting of a bacterial infection and a fungal infection. In some embodiments, the bacterial infection is caused by an infection of *Streptococcus pneumoniae*. In other embodiments the microbial infection is a fungal infection caused by an infection of an organism selected from the group consisting of *Aspergillus* species, *Fusarium* species, *Coccidiodes* species, *Cryptococcus* species, and *Histoplasma* species.

In some embodiments, the microbial infection is caused by an organism having a propensity to cause lung infection, including but not limited to, *Streptococcus* species, Gram positive bacterial species, Gram negative bacterial species, including *Pseudomonas* species, *Nocardia* species, *Actinomyces* species, Mycobacteria species as well as fungal organisms such as *Aspergillus* species, *Cryptosporidium* species, *Histoplasma* species, *Mucorales* species and *Zygomycetes* species.

In particular embodiments, at least one antibody specific for at least one polysaccharide comprising a galactofuranose residue is selected from the group consisting of monoclonal antibody 205 (MAb 205) comprising a variable heavy (VH) domain of SEQ ID NO: 1 and a variable light (VL) domain of SEQ ID NO:2; monoclonal antibody 24 (MAb 24) comprising a VH domain of SEQ ID NO:3 and a VL domain of SEQ ID NO:4; monoclonal antibody 686 (MAb 686) comprising a VH domain of SEQ ID NO:5 and a VL domain of SEQ ID NO: 6; monoclonal antibody 838 (MAb 838) comprising a VH domain of SEQ ID NO:7 and a VL domain of SEQ ID NO:8; and monoclonal antibody 476 (MAb 476) comprising a VH domain of SEQ ID NO:9 and a VL domain of SEQ ID NO:10.

One of ordinary skill in the art upon review of the presently disclosed subject matter would appreciate that any biological fluid in which at least one polysaccharide comprising a galactofuranose residue is secreted is suitable for use with the presently disclosed methods. In particular embodiments, the biological sample is selected from the group consisting of urine, bronchoalveolar lavage (BAL) fluid, serum, gastrointestinal fluids, blood, and cerebrospinal fluid (CSF).

In some embodiments, the presently disclosed methods further comprise pre-treating the biological sample before contacting the biological sample with at least one antibody specific for at least one polysaccharide comprising a galactofuranose residue. The pre-treating step can include a step selected from the group consisting of filtering, diluting, and concentrating the biological sample, and combinations thereof.

Without being held to any particular theory, the Mab476 antibody used in the methods of the present invention is thought to bind to the galF-containing O-glycan moiety/moieties associated with CelA/AspF-like protein. As described above, the Mab476 antibody may bind to galF from any origin, including galF that is present on extracellular vesicles shed by the infectious organism.

In accordance with some embodiments, the method for treating the sample in step (a) comprises contacting the sample with a substrate which binds $Ca^{2+}$ ions with high affinity.

Examples of substrates which can bind divalent cations with high affinity include, for example, N,N,N',N'-tetrakis-(2-pyridylmethyl)ethylenediamine (TPEN, membrane-permeable chelator) and diethylenetriaminepentaacetic acid (DTPA, membrane-impermeable chelator), cation exchange resins such as AG50, Chelex, poly(acrylic acid), and others, such as sepharose, for example.

In accordance with some embodiments, the method for treating the sample in step (a) comprises contacting the sample with a compound which chelates $Ca^{2+}$ ions with high affinity. Examples of chelators include, without limitation, ethylenediamine tetraacetic acid (EDTA), Ethylene glycol-bis(2-aminoethylether)-N,N,N',N'-tetraacetic acid (EGTA), 1,2-bis(o-Aminophenoxy) ethane-N,N,N',N'-tetraacetic Acid (BAPTA), 1-(2-Nitro-4,5-dimethoxyphenyl)-1,2-diaminoethane-N,N,N',N'-tetraacetic Acid, 4Na, Dimethoxynitrophenamine (DM-Nitrophen), and others.

In accordance with some embodiments, the method for treating the sample in step (a) comprises contacting the sample with EDTA and/or EGTA.

In accordance with some embodiments, the method for treating the sample in step (a) comprises contacting the sample with a substrate which binds hIntL-1 with high affinity.

Examples of compounds which bind hIntL-1 include, but are not limited to, glycerol, 3-keto-2-deoxyoctonic acid, D-glycerol-1-phosphate, D-mannoheptose, and other compounds which are bound by hIntL-1.

In accordance with some embodiments, the method for treating the sample in step (a) comprises contacting the sample with an antibody specific for hIntL-1. In some embodiments, the antibody can be rabbit polyclonal IgG anti-human INTL-1 antibody.

In accordance with some embodiments, the method for treating the sample in step (a) comprises contacting the sample with one or more compounds which are bound by hIntL-1 with high affinity.

In accordance with some embodiments, the method for treating the sample in step (a) comprises contacting the sample with one or more compounds which bind hIntL with high affinity selected from the group consisting of glycerol, 3-Keto-2-deoxyoctonic acid; D-glycerol-1-phosphate, D-mannoheptose, sepharose, sepharose-containing particles (i.e. latex, polystyrene or glass beads, microspheres or gels.

In accordance with some embodiments, the method for treating the sample in step (a) comprises a combination of one or more of the above methods including, for example, treating the sample with a chelator and one or more compounds which are bound by hIntL with high affinity, and an anti-IntL-antibody. Any of the above methods can be combined to further prevent hIntL-1 from binding galF in a biological sample.

In accordance with some embodiments, the method for treating the sample in step (a) comprises contacting the sample with a desalting column. Examples of desalting columns are known in the art, including, for example, desalting columns which are pre-packed with polyacrylamide size exclusion resins.

The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein. In particular embodiments, the subject is a human adult suspected of having, having, or susceptible of having a microbial infection. In other embodiments, the subject is a human child, e.g., a human less than about 19 years of age, suspected of having, having, or susceptible of having a microbial infection.

The presently disclosed methods can be used to diagnose, for the prognosis, or the monitoring of a disease state or condition. As used herein, the term "diagnosis" refers to a predictive process in which the presence, absence, severity or course of treatment of a disease, disorder or other medical condition is assessed. For purposes herein, diagnosis also includes predictive processes for determining the outcome resulting from a treatment. Likewise, the term "diagnosing," refers to the determination of whether a sample specimen exhibits one or more characteristics of a condition or disease. The term "diagnosing" includes establishing the presence or absence of, for example, a target antigen or reagent bound targets, or establishing, or otherwise determining one or more characteristics of a condition or disease, including type, grade, stage, or similar conditions. As used herein, the term "diagnosing" can include distinguishing one form of a disease from another. The term "diagnosing" encompasses the initial diagnosis or detection, prognosis, and monitoring of a condition or disease.

The term "prognosis," and derivations thereof, refers to the determination or prediction of the course of a disease or condition. The course of a disease or condition can be determined, for example, based on life expectancy or quality of life. "Prognosis" includes the determination of the time course of a disease or condition, with or without a treatment or treatments. In the instance where treatment(s) are contemplated, the prognosis includes determining the efficacy of a treatment for a disease or condition.

As used herein, the term "risk" refers to a predictive process in which the probability of a particular outcome is assessed. The term "monitoring," such as in "monitoring the course of a disease or condition," refers to the ongoing diagnosis of samples obtained from a subject having or suspected of having a disease or condition. The term "marker" refers to a molecule, including an antigen, such as a polysaccharide, that when detected in a sample is characteristic of or indicates the presence of a disease or condition.

Accordingly, in some embodiments, the presently disclosed subject matter provides a method for diagnosing of a microbial infection in a mammalian subject suspected of having, having, or susceptible to having a microbial infection, wherein the method comprises monitoring a treatment regimen of a microbial infection to determine the efficacy of the treatment regimen.

In accordance with some embodiments, the methods disclosed herein can be used with lateral flow devices such as those disclosed in in U.S. patent application Ser. No. 13/511,264, and incorporated by reference herein in its entirety. The presently disclosed methods can use a lateral flow device or dipstick assay comprising an immunochromatographic strip test that relies on a direct (double antibody sandwich) reaction. Without wishing to be bound to any one particular theory, this direct reaction scheme is best used when sampling for larger analytes that may have multiple antigenic sites. Different antibody combinations can be used, for example different antibodies can be included on the capture (detection) line, the control line, and included in the mobile phase of the assay, for example, as conjugated to gold particles, e.g., gold microparticles or gold nanoparticles.

In an embodiment, the present disclosure comprises kits for diagnosing a microbial infection in a biological sample from a mammalian subject suspected of having, having, or susceptible to having a microbial infection by detecting the presence of at least one polysaccharide comprising a galactofuranose residue in a biological sample of the mammalian subject. Such kits may include all necessary reagents, components, apparatus and instructions for treating the biological sample to inhibit human intelectin (hIntL) binding of galactofuranose residues present in the sample; in an embodiment, the kits may further comprise at least one antibody specific for at least one polysaccharide comprising a galactofuranose residue in an effective amount to produce a detectable amount of antibody-polysaccharide complex; in an embodiment, the kit further enables detecting the presence of at least one antibody-polysaccharide complex, wherein the detection of the presence of at least one antibody-polysaccharide complex is diagnostic of a microbial infection in a mammalian subject. In certain embodiments, the kit comprises the use of a lateral flow apparatus, dipstick, assay stick with immunochromatographic detection display, and any such apparatus know to those skilled in the art. In certain embodiments, reagents and/or detection components may be immobilized on the apparatus itself (i.e. on the dipstick). In certain embodiments, reagents for chelating calcium are included in the kit.

As used herein the term "lateral flow" refers to liquid flow along the plane of a substrate or carrier, e.g., a lateral flow membrane. In general, lateral flow devices comprise a strip (or a plurality of strips in fluid communication) of material capable of transporting a solution by capillary action, i.e., a wicking or chromatographic action, wherein different areas or zones in the strip(s) contain assay reagents, which are either diffusively or non-diffusively bound to the substrate, that produce a detectable signal as the solution is transported to or migrates through such zones. Typically, such assays comprise an application zone adapted to receive a liquid sample, a reagent zone spaced laterally from and in fluid communication with the application zone, and a detection zone spaced laterally from and in fluid communication with the reagent zone. The reagent zone can comprise a compound that is mobile in the liquid and capable of interacting with an analyte in the sample, e.g., to form an analyte-reagent complex, and/or with a molecule bound in the detection zone. The detection zone may comprise a binding molecule that is immobilized on the strip and is capable of interacting with the analyte and/or the reagent and/or an analyte-reagent complex to produce a detectable signal. Such assays can be used to detect an analyte in a sample through direct (sandwich assay) or competitive binding. Examples of lateral flow devices are provided in U.S. Pat. No. 6,194,220 to Malick et al.; U.S. Pat. No. 5,998,221 to Malick et al.; U.S. Pat. No. 5,798,273 to Shuler et al.; and RE38,430 to Rosenstein.

In some embodiments, the presently disclosed methods can be used with an assay comprising a sandwich lateral flow or dipstick assay. In a sandwich assay, a liquid sample that may or may not contain an analyte of interest is applied to the application zone and allowed to pass into the reagent zone by capillary action. The term "analyte" as used herein refers to a polysaccharide comprising a galactofuranose residue. In certain embodiments the presence or absence of an analyte in a sample is determined qualitatively. In other embodiments, a quantitative determination of the amount or concentration of analyte in the sample is determined.

The analyte, if present, interacts with a labeled reagent in the reagent zone to form an analyte-reagent complex and the analyte-reagent complex moves by capillary action to the detection zone. The analyte-reagent complex becomes trapped in the detection zone by interacting with a binding molecule specific for the analyte and/or reagent. Unbound sample can pass through the detection zone by capillary action to a control zone or an absorbent pad laterally juxtaposed and in fluid communication with the detection zone. The labeled reagent may then be detected in the detection zone by appropriate means.

Generally, and without limitation, lateral flow devices comprise a sample pad. A sample pad comprises a membrane surface, also referred to herein as a "sample application zone," adapted to receive a liquid sample. A standard cellulose sample pad has been shown to facilitate absorption and flow of biological samples, including, but not limited to, urine. The sample pad comprises a portion of lateral flow device that is in direct contact with the liquid sample, that is, it receives the sample to be tested for the analyte of interest. The sample pad can be part of, or separate from, a lateral flow membrane. Accordingly, the liquid sample can migrate, through lateral or capillary flow, from sample pad toward a portion of the lateral flow membrane comprising a detection zone. The sample pad is in fluid communication with the lateral flow membrane comprising an analyte detection zone. This fluid communication can arise through either be an overlap, top-to-bottom, or an end-to-end fluid connection between the sample pad and a lateral flow membrane. In certain embodiments, the sample pad comprises a porous material, for example and not limited to, paper. In certain embodiments the targeting agent, molecule or other reagent of the diagnostic method may be immobilized on the conjugate pad. In certain embodiments, the targeting agent, molecule or other reagent of the diagnostic method may be present in an alternative format.

The term "sample" as used herein refers to any biological sample suspected of containing an analyte for detection or a control sample expected to be substantially free of the analyte of interest. In particular embodiments, the sample comprises a biological fluid of a subject suspected of having, having, or susceptible of having a microbial infection. In some embodiments, the biological sample is in liquid form, while in other embodiments it can be changed into a liquid form, e.g., by reconstitution in a suitable solvent, e.g., an aqueous solution. The presently disclosed lateral flow devices are suitable for use with a variety of biological samples including, but not limited to, urine, bronchoalveolar lavage (BAL) fluid, serum, blood, gastrointestinal fluids, and cerebrospinal fluid (CSF).

Typically, a sample pad is positioned adjacent to and in fluid communication with a conjugate pad. A conjugate pad comprises a labeled reagent having specificity for one or more analytes of interest. In some embodiments, the conjugate pad comprises a non-absorbent, synthetic material (e.g., polyester) to ensure release of its contents. A detection conjugate is dried into place on the conjugate pad and only released when the liquid sample is applied to the sample pad. Detection conjugate can be added to the pad by immersion or spraying.

In particular embodiments, the detection conjugate comprises an antibody having specificity for a polysaccharide comprising a galactofuranose residue. In representative embodiments, the antibody is selected from the group consisting of monoclonal antibody 205 (MAb 205) comprising a variable heavy (VH) domain of SEQ ID NO:1 and a variable light (VL) domain of SEQ ID NO:2; monoclonal antibody 24 (MAb 24) comprising a VH domain of SEQ ID NO:3 and a VL domain of SEQ ID NO:4; monoclonal antibody 686 (MAb 686) comprising a VH domain of SEQ ID NO:5 and a VL domain of SEQ ID NO:6; monoclonal antibody 838 (MAb 838) comprising a VH domain of SEQ ID NO:7 and a VL domain of SEQ ID NO: 8; and monoclonal antibody 476 (MAb 476) comprising a VH domain of SEQ ID NO:9 and a VL domain of SEQ ID NO:10. The antibody, e.g., a monoclonal antibody (MAb), can be conjugated to a gold particle, e.g., colloidal gold, including igold microspheres or gold nanoparticles, such as gold nanoparticles of about 40 nm. For example, it is possible to biotinylate the conjugated MAb to take advantage of the strong affinity that biotin has for streptavidin, using Streptavidin-coated microspheres. Alternatives include protein A-coated microspheres that bind to Fc region of IgGs. Conditions to define optimal optimization to colloidal gold can be determined, for example, in microtiter wells. For example, 100 μL of colloidal gold at 1 OD530 can be added to each well, followed by 10 μL of 22 mM buffers (MES, HEPES) at variable pH (5.5 to 10, in 0.5 increments). Antibodies can be added at concentrations ranging from about 1.25 μg/1 OD colloid to about 10 μg/1 OD colloid, incubated for 15 minutes, and then 25 μL of 1.5 NaCl can be added. Conjugated particles will be stable and pink; the optimal condition that requires the lowest concentration of antibodies can be determined.

Usually, the conjugate pad is adjacent to and in fluid communication with a lateral flow membrane. Capillary action draws a fluid mixture up the sample pad, through the conjugate pad where an antibody-polysaccharide complex is formed, and into the lateral flow membrane. Lateral flow is a function of the properties of the lateral flow membrane. The lateral flow membrane typically is extremely thin and is hydrophilic enough to be wetted, thereby permitting unimpeded lateral flow and mixture of reactants and analytes at essentially the same rates.

Lateral flow membranes can comprise any substrate capable of providing liquid flow including, but not limited to, substrates, such as nitrocellulose, nitrocellulose blends with polyester or cellulose, untreated paper, porous paper, rayon, glass fiber, acrylonitrile copolymer, plastic, glass, or nylon. Lateral flow membranes can be porous. Typically, the pores of a lateral flow membrane are of sufficient size such that particles, e.g., microparticles comprising a reagent capable of forming a complex with an analyte, flow through the entirety of the membrane. Lateral flow membranes, in general, can have a pore size ranging from about 3 μm to about 100 μm, and, in some embodiments, have a pore size ranging from about 10 μm to about 50 μm. Pore size affects capillary flow rate and the overall performance of the device.

There are multiple benefits to using nitrocellulose for the primary membrane: low cost, capillary flow, high affinity for protein biding, and ease of handling. Nitrocellulose has high protein binding. Another alternative is cellulose acetate, which has low protein binding. Size dictating surface area dictates membrane capacity (the volume of sample that can pass through the membrane per unit time=length×width×thickness×porosity. Because these variables control the rate at which lateral flow occurs, they can impact sensitivity and specificity of the assay. The flow rate also varies with sample viscosity. Several different sizes and polymers are available for use as microspheres, which migrate down the membrane with introduction of the fluidic sample. The optimal flow rate generally is achieved using spheres that are 1/10 the pore size of the membrane or smaller.

One skilled in the art will be aware of other materials that allow liquid flow. Lateral flow membranes, in some embodiments, can comprise one or more substrates in fluid communication. For example, a conjugate pad can be present on the same substrate or may be present on separate substrates (i.e., pads) within or in fluid communication with lateral flow membranes. In some embodiments, the nitrocellulose membrane can comprise a very thin Mylar sheet coated with a nitrocellulose layer.

Lateral flow membranes can further comprise at least one indicator zone or detection zone. The terms "indicator zone" and "detection zone" are used interchangeably herein and mean the portion of the carrier or porous membrane comprising an immobilized binding reagent. As used herein, the term "binding reagent" means any molecule or a molecule bound to a particle, wherein the molecule recognizes or binds the analyte in question. The binding reagent is capable of forming a binding complex with the analyte-labeled reagent complex. The binding reagent is immobilized in the detection zone and is not affected by the lateral flow of the liquid sample due to the immobilization on the membrane. Once the binding reagent binds the analyte-labeled reagent complex it prevents the analyte-labeled reagent complex from continuing with the flow of the liquid sample. In some embodiments, the binding reagent is an antibody having specificity for a polysaccharide having at least one galactofuranose residue.

Accordingly, during the actual reaction between the analyte and the reagent, the first member binds in the indicator zone to the second member and the resulting bound complex is detected with specific antibodies. Detection may use any of a variety of labels and/or markers, e.g., enzymes (alkaline phosphatase or horseradish peroxidase with appropriate substrates), radioisotopes, liposomes or latex beads impregnated with fluorescent tags, polymer dyes or colored particles, and the like. Thus, the result can be interpreted by any direct or indirect reaction. Colloidal gold particles, which impart a purple or red coloration, are most commonly used currently.

The capture and immobilization of the assay reagent (complementary member of the binding pair) at the indicator zone can be accomplished by covalent bonding or, more commonly, by adsorption, such as by drying. Such capture also can be indirect, for example, by binding of latex beads coated with the reagent. Depending on the nature of the material comprising the lateral flow membrane, covalent bonding may be enabled, for example with use of glutaraldehyde or a carbodiimide. In immunoassays, most common binding pairs are antigen-antibody pairs; however, multiple other binding pairs can be performed, such as enzyme-substrate and receptor-ligand.

In some embodiments, the indicator zone further comprises a test line and a control line. A test line can comprise an immobilized binding reagent. When antibodies are used to develop a test line in the LFD that employs a sandwich type of assay, they are applied at a ratio of about 1-3 μg/cm across the width of a strip 1 mm wide; hence, antibody concentration is about 10-30 μg/$cm^2$, which is about 25-100 fold that used in an ELISA. Brown, M. C., *Antibodies: key to a robust lateral flow immunoassay, in Lateral Flow Immunoassay*, H. Y. T. R. C. Wong, Editor. 2009, Humana Press: New York, New York. p. 59-74.

Further, in some embodiments, the presently disclosed lateral flow assays can be used to detect multiple analytes in a sample. For example, in a lateral flow assay, the reagent zone can comprise multiple labeled reagents, each capable of binding to a different analyte in a liquid sample or a single labeled reagent capable of binding to multiple analytes. If multiple labeled reagents are used in a lateral flow assay, the reagents may be differentially labeled to distinguish different types of analytes in a liquid sample.

It also is possible to place multiple lines of capture antibodies on the membrane to detect different analytes. Combinations of antibodies that detect different epitopes of glycans may optimize specificity if it is found that one antibody performs at a low quantitative limit of detection, yet exhibits some degree of nonspecific binding (or binding to urine components in control animals). One possibility is that the device may be adapted to detect galF and another fungal component to increase the potential spectrum of pathogens detected and to increase specificity of the reaction. *Aspergillus* species are thought to secrete galF and other fungal components, while glycans from other 'contaminants' should not contain other fungal components.

For quality control, typically a lateral flow membrane can include a control zone comprising a control line. The term "control zone" refers to a portion of the test device comprising a binding molecule configured to capture the labeled reagent. In a lateral flow assay, the control zone may be in liquid flow contact with the detection zone of the carrier, such that the labeled reagent is captured on the control line as the liquid sample is transported out of the detection zone by capillary action. Detection of the labeled reagent on the control line confirms that the assay is functioning for its intended purpose. Placement of a control line can be accomplished using a microprocessor controlled TLC spotter, in which a dispenser pump releases a constant volume of reagent across the membrane.

A typical lateral flow device can also comprises an absorbent pad. The absorbent pad comprises an "absorbent material," which as used herein, refers to a porous material having an absorbing capacity sufficient to absorb substantially all the liquids of the assay reagents and any wash solutions and, optionally, to initiate capillary action and draw the assay liquids through the test device. Suitable absorbent materials include, for example, nitrocellulose, nitrocellulose blends with polyester or cellulose, untreated paper, porous paper, rayon, glass fiber, acrylonitrile copolymer, plastic, glass, or nylon.

In some embodiments, a lateral flow membrane is bound to one or more substantially fluid-impervious sheets, one on either side, e.g., a bottom sheet and a complimentary top sheet with one or more windows defining an application zone and an indicator zone.

A typical lateral flow device also can include a housing. The term "housing" refers to any suitable enclosure for the presently disclosed lateral flow devices. Exemplary housings will be known to those skilled in the art. The housing can have, for example, a base portion and a lid portion. The lid portion can include a top wall and a substantially vertical side wall. A rim may project upwardly from the top wall and may further define a recess adapted to collect a sample from a subject. Suitable housings include those provided in U.S. Pat. No. 7,052,831 to Fletcher et al and those used in the BD Directigen™ EZ RSV lateral flow assay device.

As with the general method described immediately hereinabove, the microbial infection can be selected from the group consisting of a bacterial infection and a fungal infection. In some embodiments, the bacterial infection is caused by an infection of *Streptococcus pneumoniae*. In particular embodiments, the microbial infection is a fungal infection caused by an infection of an organism selected from the group consisting of *Streptococcus pneumoniae, Aspergillus species, Fusarium species, Coccidioides species, Cryptococcus species*, and *Histoplasma* species.

In some embodiments, the microbial infection is caused by an organism having a propensity to cause lung infection, including but not limited to, *Streptococcus* species, Gram positive bacterial species, Gram negative bacterial species, including *Pseudomonas* species, *Nocardia* species, *Actinomyces* species, Mycobacteria species as well as fungal organisms such as *Aspergillus* species, *Cryptosporidium* species, *Histoplasma* species, *Pneumocystis* species, *Mucorales* species and *Zygomycetes* species.

In some embodiments, a polysaccharide having a galactofuranose residue can be measured in whole, unconcentrated, or otherwise unprocessed, biological samples using the presently disclosed methods and devices. In other embodiments, the biological sample can be processed, e.g., concentrated, diluted, filtered, and the like, prior to performing the test. The pre-treatment of the urine sample can include diluting the urine sample in an aqueous solution, concentrating the urine sample, filtering the urine sample, or a combination thereof.

One of ordinary skill in the art upon review of the presently disclosed subject matter would appreciate that the pre-treatment steps can be performed in any particular order, e.g., in some embodiments, the sample can be diluted or concentrated and then filtered, whereas in other embodiments, the sample can be filtered and then diluted or concentrated. In particular embodiments, the presently disclosed methods include filtering the urine sample, for example, through a desalting column, to remove an inhibitor that interferes with the detection of antigen in the urine sample. This step can be performed with or without any further dilution or concentration of the sample.

Thus, in some embodiments, the lateral flow device further comprises an apparatus adapted to pre-treat the biological sample before contacting the biological sample with at least one antibody specific for at least one polysaccharide comprising a galF residue. In particular embodiments, the apparatus is adapted to filter, dilute, or concentrate the biological sample, or combinations thereof. More particularly, the apparatus can be adapted to remove an inhibitor that interferes with the detection of the at least one polysaccharide comprising a galF residue in the biological sample, in particular, a urine sample.

In other embodiments, different parameters of the test, e.g., incubation time, can be manipulated to increase sensitivity and/or specificity of the test to eliminate the need for processing the biological sample. Accordingly, in some embodiments, the presently disclosed subject matter provides an antibody specific for at least epitope of a polysaccharide secreted by a microbial organism. In particular embodiments, the polysaccharide comprises a galF residue. In more particular embodiments, the antibody is specific for at least one epitope of a polysaccharide secreted by a microbial organism selected from the group consisting of *Aspergillus* species, *Fusarium* species, *Coccidioides* species, *Cryptococcus* species, *Histoplasma* species, and certain *Streptococcus* species. In additional embodiments, the antibody is specific for at least one epitope of a polysaccharide secreted by a microbial organism selected from the group consisting of *Streptococcus* species, Gram positive bacterial species, Gram negative bacterial species, including *Pseudomonas* species, *Nocardia* species, *Actinomyces* species, Mycobacteria species as well as fungal organisms such as *Aspergillus* species, *Cryptosporidium* species, *Histoplasma* species, *Pneumocystis* species, *Mucorales* species and *Zygomycetes* species.

Also provided herein are kits comprising components of a diagnostic regimen, for example components for processing a sample along with a detection assay, lateral flow device, dipstick, and instructions for using the same. The kit can also comprise packaging or a container housing at least one or more components of the diagnostic assay, and can also comprise instructions on storage, administration, dosing or the like and/or an insert regarding the active ingredients. The kit can also comprise instructions for monitoring the presence and/or prevalence of an infectious organisms (or metabolites thereof) once administered, and optionally, materials for performing such assays including, e.g., reagents, well plates, containers, markers or labels, and the like. Other suitable components to include in kits of the disclosure will be readily apparent to one of skill in the art, taking into consideration the infectious organism to be detected, sample to be processed, and storage conditions.

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following examples have been included to provide guidance to one of ordinary skill in the art for practicing representative embodiments of the presently disclosed subject matter. In light of the present disclosure and the general level of skill in the art, those of skill can appreciate that the following examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example

Characterization of mAb476-Reactive Galactofuranose (Galf)-Bearing *Aspergillus* Antigens Excreted in Urine Urine antigen testing is commonly used for different fungal infections (cryptococcosis, histoplasmosis) and the inventors have previously demonstrated proof of concept in animal models and human samples for urine diagnostics for multiple Ascomycetes (+aspergillosis) using a novel monoclonal Ab that rapidly localizes to the urine in infected animals. Currently, enzyme immunoassays (ELISA) and lateral flow devices (LFD) are in advanced stages of development. The prototypes have sensitivity/specificity approximating 80-90% as early aid to diagnose invasive pulmonary aspergillosis (IPA).

Background. The inventors previously described a novel monoclonal antibody (mAb476) that is specific to *Aspergillus* Galactofuranose (Galf)-bearing glycoconjugates in ethanol precipitated fraction of culture supernatants. Animal models revealed that the systemically administered antibody rapidly localized to the urinary bladder in animals that were infected with *A. fumigatus* in the lung. Proof of concept for use of mAb476 as an aid to diagnose invasive aspergillosis (IA) has been demonstrated in a lateral flow dipstick assay. Given novelty of urine diagnostic testing for invasive aspergillosis and to understand antibody specificity and mechanism(s) of renal antigen excretion, the inventors investigated the nature of mAb476-reactive antigens in microbial and clinical samples.

Methods. mAb476 epitope specificity was determined by ELISA screening against Galf-containing glycoconjugates. The physical nature of immunoreactive antigens in both microbial and clinical samples was characterized by differential ultracentrifugation with nanoparticle tracking analysis and transmission electron microscopy (TEM). mAb476-reactive urine antigens were identified in two representative patients with documented IA by western blotting and immunoprecipitation followed by mass spectrometry.

- mAb476 specificity to purified galactomannan (GM) and ethanol precipitate (EP) compared to EB-A2 (extracted from Platelia kit)
- mAb476 galf epitope specificity characterized using ELISA (galf-conjugated BSA)
- mAb476 immunoprecipitation with mass spectrophotometry performed on two reactive patient urines
- Physical nature of antigen characterized As shown in the figures and explained in detail below, mAb476 has novel specificity for polysaccharides in EP.

Results. In ELISA, mAb476 recognized monomeric Galf, as well as disaccharide Galf-β-(1→5)-Galf, and oligosaccharide ligands with three or more Galf-β-(1→5) units. Immunofluorescence and TEM revealed antibody binding to both conidial and hyphal cell walls. Culture supernatant immunoreactivity was in both extracellular vesicle (EV, 40-200 nm) and EV-depleted fractions. TEM confirmed microbial mAb476-reactive cellular and secreted EVs. Similar mAb476-reactive EVs were observed in urine from patients with IA. Western blots demonstrated one or more mAb476-reactive 20-30 kDa bands; mass spectrometry of mAb476-immunoprecipitated material revealed prominent fungal O-glycated cellulase and membrane, metabolic and housekeeping proteins consistent with EV cargo.

Conclusions. mAb476 demonstrates unique recognition of terminal Galf monomers exposed on *Aspergillus* cellular and secreted glycoproteins. Both microbial and clinical samples contain immunoreactive fractions within EVs, suggesting that physiologic renal clearance of fungal Galf-bearing EVs has potential for clinical diagnostic applications.

All references, including publications, patent applications, and patents, cited herein are hereby incorporated by reference to the same extent as if each reference were individually and specifically indicated to be incorporated by reference and were set forth in its entirety herein.

The use of the terms “a” and “an” and “the” and similar referents in the context of describing the invention (especially in the context of the following claims) are to be construed to cover both the singular and the plural, unless otherwise indicated herein or clearly contradicted by context. The terms “comprising,” “having,” “including,” and “containing” are to be construed as open-ended terms (i.e., meaning “including, but not limited to,”) unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., “such as”) provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed:

1. A method for detecting galactofuranose present on extracellular vesicles from a fungus in a urine sample from a subject, wherein the urine sample is suspected of containing the extracellular vesicles from the fungus;

said method comprising:

(a) processing the urine sample thereby producing a processed urine sample, wherein said processing comprises contacting the urine sample with a sufficient amount of a substrate to reduce human intelectin (hIntL) binding to the galactofuranose present on the extracellular vesicles from the fungus in the urine sample, wherein the substrate comprises
   (i) a desalting column,
   (ii) a compound which chelates divalent cations, or
   (iii) a substrate that disables galactofuranose recognition by intelectin selected from the group consisting of glycerol, 3-Keto-2-deoxyoctonic acid; D-glycerol-1-phosphate, D-mannoheptose, sepharose, and sepharose-containing particles;

(b) using a detection assay to detect the presence of the extracellular vesicles from the fungus, wherein the detection assay comprises contacting the processed urine sample with at least one antibody that binds to the galactofuranose, wherein the at least one antibody comprises a heavy chain complementarity-determining region 1 (HCDR1), a HCDR2, and a HCDR3 and a light chain complementarity-determining region 1 (LCDR1), a LCDR2, and a LCDR3 of an antigen binding domain of an antibody selected from the group consisting of antibody 205 (mAb205), antibody 24 (mAb24), antibody 686 (mAb686), antibody 838 (mAb838), and antibody 476 (mAb476), wherein:
   (i) the antibody 205 (mAb205) comprises a heavy chain encoded by the sequence according to SEQ ID NO: 1 and a light chain encoded by the sequence according to SEQ ID NO: 2,
   (ii) the antibody 24 (mAb24) comprises a heavy chain encoded by the sequence according to SEQ ID NO: 3 and a light chain encoded by the sequence according to SEQ ID NO: 4,
   (iii) the antibody 686 (mAb686) comprises a heavy chain encoded by the sequence according to SEQ ID NO: 5 and a light chain encoded by the sequence according to SEQ ID NO: 6,
   (iv) the antibody 838 (mAb838) comprises a heavy chain encoded by the sequence according to SEQ ID NO: 7 and a light chain encoded by the sequence according to SEQ ID NO: 8, and
   (v) the antibody 476 (mAb476) comprises a heavy chain encoded by the sequence according to SEQ ID NO: 9 and a light chain encoded by the sequence according to SEQ ID NO: 10; and (c) detecting the presence of a complex comprising the at least one antibody and the galactofuranose; wherein the presence of the complex is indicative of the presence of the extracellular vesicles from the fungus in the urine sample.

2. The method of claim 1, wherein the substrate comprises the desalting column.

3. The method of claim 1, wherein the substrate comprises the compound which chelates divalent cations.

4. The method of claim 1, wherein the substrate comprises the substrate that disables galactofuranose recognition by intelectin selected from the group consisting of glycerol, 3-Keto-2-deoxyoctonic acid; D-glycerol-1-phosphate, D-mannoheptose, sepharose, and sepharose-containing particles.

5. The method of claim 4, wherein the sepharose-containing particles comprise one or more of latex, polystyrene or glass beads, microspheres and gels.

6. The method of claim 1, wherein the at least one antibody comprises a variable heavy domain (VH) and a variable light chain domain (VL) of an antibody selected from the group consisting of antibody 205 (mAb205), antibody 24 (mAb24), antibody 686 (mAb686), antibody 838 (mAb838), and antibody 476 (mAb476), wherein:

(i) the antibody 205 (mAb205) comprises a heavy chain encoded by the sequence according to SEQ ID NO: 1 and a light chain encoded by the sequence according to SEQ ID NO: 2, (ii) the antibody 24 (mAb24) comprises a heavy chain encoded by the sequence according to SEQ ID NO: 3 and a light chain encoded by the sequence according to SEQ ID NO: 4, (iii) the antibody 686 (mAb686) comprises a heavy chain encoded by the sequence according to SEQ ID NO: 5 and a light chain encoded by the sequence according to SEQ ID NO: 6, (iv) the antibody 838 (mAb838) comprises a heavy chain encoded by the sequence according to SEQ ID NO: 7 and a light chain encoded by the sequence according to SEQ ID NO: 8, and (v) the antibody 476 (mAb476) comprises a heavy chain encoded by the sequence according to SEQ ID NO: 9 and a light chain encoded by the sequence according to SEQ ID NO: 10.

7. The method of claim 1, wherein the detection of the extracellular vesicles from the fungus is diagnostic of the presence of the fungus in a body, and wherein the fungus is selected from the group consisting of: *Aspergillus* spp, *Aspergillus fumigatuss, Aspergillus flavus, Aspergillus niger, Aspergillus nidulans, Aspergillus terreus, Aspergillus sydowi, Aspergillus glaucus, Fusarium, Scedosporium, Histoplasma, Coccidioides, Paracoccidioides, Blastomyces, Pseudallescheria, Fusarium, Trichophyton, Trichosporon, Microsporum, Epidennophyton, Scytalidium, Malassezia, Penicillium*, and *Pneumocystis*.

8. The method of claim 7, wherein the fungus is an *Aspergillus* spp.

9. The method of claim 3, wherein the compound which chelates divalent cations comprises ethylenediamine tetraacetic acid (EDTA), Ethylene glycol-bis(2-aminoethylether)-N,N,N',N'-tetraacetic acid (EGTA), 1,2-bis(o-Aminophenoxy) ethane-N,N,N',N'-tetraacetic Acid (BAPTA), 1-(2-Nitro-4,5-dimethoxyphenyl)-1,2-di aminoethane-N,N,N',N'-tetraacetic Acid, 4Na, or Dimethoxynitrophenamine (DM-Nitrophen).

10. The method of claim 3, wherein the compound which chelates divalent cations comprises EDTA or EGTA.

11. The method of claim 6, wherein the at least one antibody comprises an antibody selected from the group consisting of antibody 205 (mAb205), antibody 24 (mAb24), antibody 686 (mAb686), antibody 838 (mAb838), and antibody 476 (mAb476), wherein:

(i) the antibody 205 (mAb205) comprises a heavy chain encoded by the sequence according to SEQ ID NO: 1 and a light chain encoded by the sequence according to SEQ ID NO: 2, (ii) the antibody 24 (mAb24) comprises a heavy chain encoded by the sequence according to SEQ ID NO: 3 and a light chain encoded by the sequence according to SEQ ID NO: 4, (iii) the antibody 686 (mAb686) comprises a heavy chain encoded by the sequence according to SEQ ID NO: 5 and a light chain encoded by the sequence according to SEQ ID NO: 6, (iv) the antibody 838 (mAb838) comprises a heavy chain encoded by the sequence according to SEQ ID NO: 7 and a light chain encoded by the sequence according to SEQ ID NO: 8, and (v) the antibody 476 (mAb476) comprises a heavy chain encoded by the sequence according to SEQ ID NO: 9 and a light chain encoded by the sequence according to SEQ ID NO: 10.

12. The method of claim 1, wherein the at least one antibody comprises the heavy chain complementarity-determining region 1 (HCDR1), the HCDR2, and the HCDR3 and the light chain complementarity-determining region 1 (LCDR1), the LCDR2, and the LCDR3 of an antigen binding domain of the antibody 476 (mAb476), wherein the antibody 476 (mAb476) comprises the heavy chain encoded by the sequence according to SEQ ID NO: 9 and the light chain encoded by the sequence according to SEQ ID NO: 10.

13. The method of claim 12, wherein the at least one antibody comprises a variable heavy domain (VH) and a variable light chain domain (VL) of the antibody 476 (mAb476), wherein the antibody 476 (mAb476) comprises the heavy chain encoded by the sequence according to SEQ ID NO: 9 and the light chain encoded by the sequence according to SEQ ID NO: 10.

14. The method of claim 13, wherein the at least one antibody comprises the antibody 476 (mAb476), wherein the antibody 476 (mAb476) comprises the heavy chain encoded by the sequence according to SEQ ID NO: 9 and the light chain encoded by the sequence according to SEQ ID NO: 10.

* * * * *